US005654137A

United States Patent [19]
Aström et al.

[11] Patent Number: 5,654,137
[45] Date of Patent: Aug. 5, 1997

[54] HUMAN CRABP-I AND CRABP-II

[75] Inventors: Anders Aström; John J. Voorhees; Ulrika Pettersson; Amir Tavakkol, all of Ann Arbor, Mich.

[73] Assignee: The Regents Of The University Of Michigan, Ann Arbor, Mich.

[21] Appl. No.: 468,709

[22] Filed: Jun. 6, 1995

Related U.S. Application Data

[62] Division of Ser. No. 241,664, May 11, 1994, which is a continuation of Ser. No. 874,847, Apr. 28, 1992, abandoned, which is a continuation-in-part of Ser. No. 751,893, Aug. 30, 1991, abandoned.

[51] Int. Cl.⁶ .............................. C12Q 1/70; C12Q 1/68; C12N 5/10
[52] U.S. Cl. .................................... 435/5; 435/6; 435/371
[58] Field of Search .......................... 435/5, 6, 240.1, 435/240.2, 320.1; 536/23.5, 24.1, 24.31

[56] References Cited

U.S. PATENT DOCUMENTS 4,981,784  1/1991  Evans et al. ........................... 435/6

OTHER PUBLICATIONS

Antras, J., et al., "Adipsin Gene Expression in 3T3–F442A Adipocytes Is Posttranscriptionally Down–Regulated by Retinoic Acid," *J. Biol. Chem.* 266:1157–1161 (1991).

Asselineau, D., et al., "Retinoic Acid Improves Epidermal Morphogenesis," *Devel. Biol.* 133:322–335 (1989).

Astrom, A., et al., "Cloning of CRABPII cDNA from Human Skin: Retinoic Acid Induces Expression of CRABPII but Not CRABPI in Human Skin in Vivo and in Dermal but Not Lung Fibroblasts in Vitro," *J. Invest. Dermatol.* 96:547 (1991).

Astrom, A., et al., "Retinoic Acid And Synthetic Analogs Differentially Activate Retinoic Acid Receptor Dependent Transcription," *Biochem. Biophys. Res. Comm.* 173:339–345 (1990).

Astrom, A., et al., "Molecular Cloning of Two Human Cellular Retinoic Acid–binding proteins (CRABP)," *J. Biol. Chem.* 266:17662–17666 (1991).

Astrom, A., et al., "Structure of the Human Cellular Retinoic Acid–Binding Protein II (CRABP-II) Gene: Early Transcriptional Regulation by Retinoic Acid," *J. Biol. Chem.* 267:25251–25255 (1992).

Bailey, J.S. et al., "Purification and Partial Characterization of a Novel Binding Protein for Retinoic Acid from Neonatal Rat," *J. Biol. Chem.* 263:9326–9332 (1988).

Benbrook, D., et al., "A New Retinoic Acid Receptor Identified from a Hepatocellular Carcinoma," *Nature* 333:669–672 (1988).

Berghard, A, et al., "Serum and Extracellular Calcium Modulate Induction of Cytochrome P 450IA1 in Human Keratinocytes," *J. biol. Chem.* 265:21086–21090 (1990).

Bossche, H. et al., "Cytochrome–P–450–Dependent Metabolism of Retinoic Acid in Rat Skin Microsomes: Inhibition by Ketoconazole," *Skin Pharmaco.* 1:176–185 (1988).

Boyce, S.T. et al., "Chapter 13: Normal Human Epidermal Keratinocytes," in *In Vitro Models for Cancer Research* (Weber, M.M., and Sekely, L.L., eds) vol. 3, pp. 245–274. CRC Press, Boca Raton, FL (1986).

Brand, N. et al., "Identification of a Second Human Retinoic Receptor," *Nature* 332:850–853 (1988).

Busch, C. et al., "Tissue Distribution of Cellular Retinol–Binding Protein and Cellular Retinoic Acid–Binding Protein: Use of Monospecific Antibodies for Immunohistochemistry and cRNA for in Situ Localization of mRNA," *Meth. Enzymol.* 189:315–324 (1990).

Cleveland, D.W. et al., "Multiple Determinants of Eukaryotic mRNA Stability," *New. Biol.* 1:121–126 (1989).

Danielson, P.E. et al., "p1B15: A cDNA Clone of the Rat mRNA Encoding Cyclophilin," *DNA* 7:261–267 (1988).

Darmon, M. et al., "Biological Activity of Retinoids Correlates with Affinity for Nuclear Receptors but Not for Cytosolic Binding Protein," *Skin Pharmacol.* 1:161–175 (1988).

DeThe, H. et al., "Differential expression and ligand regulation of the retinoic acid receptor α and β genes," *EMBO J.* 8:429–433 (1989).

DeThe, H. et al., "Identification of a Retinoic Acid Rsponsive Element in the Retinoic Acid Receptor β Gene," *Nature* 343:177–180 (1990).

Edwards, S.A. et al., "The Transcription Factor Egr–1 Is Rapidly Modulated in Response to Retinoic Acid in P19 Embryonal Carcinoma Cells," *Dev. Biol.* 148:165–173 (1991).

Eichele, G., "Retinoids and Vertebrate Limb Pattern Formation," *Trends Genet.* 5:246–251 (1989).

Elder, J.T. et al., "Retinoic Acid Receptor Gene Expression in Human Skin," *J. Invest. Dermatol.* 96:425–433 (1991).

Elder, J.T. et al., "Protooncogene Expression in Normal and Psoriatic Skin," *J. Invest. Dermatol.* 94:19–25 (1990).

(List continued on next page.)

*Primary Examiner*—Mindy Fleisher
*Assistant Examiner*—Terry A. McKelvey
*Attorney, Agent, or Firm*—Harness, Dickey & Pierce, P.L.C.

[57] ABSTRACT

The sequences encoding two isoforms of human cellular retinoid acid binding proteins, CRABP-I and CRABP-II, have been cloned and sequenced and are set forth with their corresponding amino acid sequences. The identification of human CRABP nucleic and amino acid sequences provides the basis for the construction of recombinant human CRABP vectors and expression constructs. Human CRABP can also be synthesized or produced ex vivo, e.g. in bacterial or other production systems. Ligand binding assays, including recombinant and chimeric receptor reporter assays, and direct and competition hybridization assays employing the human CRABP sequences herein described can be used to test drugs for retinoid induction and tissue specificity for pathologies in which retinoids are implicated. Immunoassays utilizing antibodies or binding fragments produced to human CRABP can also be used to test patient tissues for the presence and levels of CRABP for diagnosis and to monitor treatment. The identification of the nucleic and amino acids sequences for human CRABP-I and CRABP-II also contributes to the elucidation of the function and interaction of the retinoid-binding proteins.

7 Claims, 17 Drawing Sheets

OTHER PUBLICATIONS

Feinberg, A.P. et al., "A Technique for Radiolabelling DNA Restriction Endonuclease Fragments to High Specific Activity," *Anal. Biochem.* 132:6–13 (1983).

Fiorella, P.D. et al., "Expression of Cellular Retinoic Acid Binding Protein (CRABP) in *Escherichia coli*," *J. Biol. Chem.* 266:16572–16579 (1991).

Floyd, E.E. et al., "Regulation of Type I (Epidermal) Transglutaminase mRNA Levels during Squamous Differentiation: Down Regulation by Retinoids," *Mol. Cell Biol.* 9:4846–4851 (1989).

Gassman, M. et al., "Efficient Production of Chicken Egg Yolk Antibodies Against a Conserved Mammalian Protein," *FASEB* 4:2528–2532 (1990).

Giguere, V. et al., "Identification of a Receptor for the Morphogen Retinoic Acid," *Nature* 330:624–629 (1987).

Giguere, V. et al., "Molecular Cloning of cDNA Encoding a Second Cellular Retinoic Acid–Binding Protein," *PNAS (USA)* 87:6233–6237 (1990).

Glass, C.K et al., "Positive and Negative Regulation of Gene Transcription by a Retinoic Acid–Thyroid Hormone Receptor Heterodimer," *Cell* 59:697–708 (1989).

Greenberg, M.E. et al., "Stimulation of 3T3 Cells Induces Transcription of the C–fos Proto–Oncogene," *Nature* 311:433–438 (1984).

Harper, R.A. et al., "Human Skin Fibroblasts Derived from Papillary and Reticular Dermis: Differences in Growth Potential in vitro," *Science* 204:526–527 (1979).

Heyman, R.A. et al., "9–Cis Retinoic Acid Is a High Affinity Ligand for the Retinoid X Receptor," *Cell* 68:397–406 (1992).

Hirschel–Scholz, S. et al., "Ligand–Specific and Non–Specific In Vivo Modulation of Human Epidermal Cellular Retinoic Acid Binding Protein (CRABP)," *Eur. J. Clin. Invest.* 19:220–227 (1989).

Kadonaga, J.T. et al., "Promoter–Specific Activation of RNA Polymerase II Transcription by Sp1," *Trends Biochem. Sci.* 11:20–23 (1986).

Kitamoto, J. et al., "The Presence of a Novel Cellular Retinoic Acid–Binding Protein in Chick Embryos: Purification an partial Characterization," *Biochem. Biophys. Res. Comm.* 157:1302–1308 (1988).

Kopan, R. et al., "The Use of Retinoic Acid to Probe the Relation Between Hyperproliferation–Associated Keratins and Cell Proliferation in Normal and Malignant Epidermal Cells," *J. Cell Biol.* 109:295–307 (1989).

Krust, A. et al., "A Third Human Retinoic Acid Receptor, hRAR-γ," *PNAS (USA)* 86:5310–5314 (1989).

Leask, A. et al., "Transcription Factor AP2 and its Role in Epidermal–Specific Gene Expression," *PNAS (USA)* 88:7948–7952 (1991).

Leid, M. et al., "Purification, Cloning, and RXR Identity of the HeLa Cell Factor with Which RAR or TR Heterodimerizes to Bind Target Sequences Efficiently," *Cell* 68:377–395 (1992).

Lemaire, P. et al., "The Serum–Inducible Mouse Gene Krox–24 Encodes a Sequence–Specific Transcriptional Activator," *Mol. Cell. Biol.* 10:3456–3467 (1990).

Levin, A.A. et al., "9–Cis Retinoic Acid Stereoisomer Binds and Activates the Nuclear Receptor RXRα," *Nature* 355:359–361 (1992).

Li, E. et al., "Rat Cellular Retinol–Binding Protein II: Use of a Cloned cDNA to Define its Primary Structure, Tissue–Specific Expression, and Developmental Regulation," *PNAS (USA)* 83:5779–5783 (1986).

Lippman, S.M. et al., "Results of the Use of Vitamin A and Retinoids in Cutaneous Malignancies," *Pharmacol. Ther.* 40:107–122 (1989).

Luckow, B. et al., "CAT Constructions with Multiple Unique Restriction Sites for the Functional Analysis of Eukaryotic Promoters and Regulatory Elements," *Nucleic Acids Res.* 15:5490 (1987).

Luscher, B. et al., "Regulation of Transcription Factor AP–2 by the Morphogen Retinoic Acid and by Second Messengers," *Genes Dev.* 3:1507–1517 (1989).

Maden, M. et al., "Spatial Distribution of Cellular Protein Binding to Retinoic Acid in the Chick Limb Bud," *Nature* 335:733–735 (1988).

Mangelsdorf, D.J. et al., "Nuclear Receptor that Identifies a Novel Retinoic Acid Response Pathway," *Nature* 345:224–229 (1990).

Mangelsdorf, D.J. et al., "A Direct Repeat in the Cellular Retinol–Binding Protein Type II Gene Confers Differential Regulation by RXR and RAR," *Cell* 66:555–561 (1991).

Mangelsdorf, D.J. et al., "Characterization of Three RXR Genes that Mediate the Action of 9–cis Retinoic acid," *Genes Dev.* 6:329–344 (1992).

Maniatis, T. et al., *Molecular Cloning. A Laboratory Manual* (1982), pp. v–ix.

Mitchell, P.J. et al., "Positive and Negative Regulation of Transcription In Vitro: Enhancer–Binding Protein AP–2 Is Inhibited by SV40 T Antigen," *Cell* 50:847–861 (1987).

Nervi, C. et al., "Expression of Nuclear Retinoic Acid Receptors in Wild–type and Mutant Embryonical Carcinoma PCC4.aza1R Cells," *Cell Growth Diff.* 1:535–542 (1990).

Nilsson, M.H.L et al., "Isolation and Characterization of a cDNA Clone Corresponding to Bovine Cellular Retinoic–Acid–Binding Protein and Chromosomal Localization of the Corresponding Human Gene," *Eur. J. Biochem.* 173:45–51 (1988).

O'Donell, A.L et al., "Thyroid Hormone Receptor Mutations that Interfere with Transcriptional Activation also Interfere with Receptor Interaction with a Nuclear Protein," *Mol. Endocrinol.* 5:94–99 (1991).

Ong, D.E. et al., "Esterification of Retinol in Rat Liver," *J. Biol. Chem.* 263:5789–5796 (1988).

Petkovich, M. et al., "A Human Retinoic Acid Receptor Which Belongs to the Family of Nuclear Receptors," *Nature* 330:444–450 (1987).

Pillai, S. et al., "Calcium Regulation of Growth and Differentiation of Normal Human Keratinocytes: Modulation of Differentiation Competence by Stages of Growth and Extracellular Calcium," *J. Cell. Physiol.* 143:294–302 (1990).

Posnett, D.N. et al., "Multiple Antigenic Peptide Method for Producing Antipeptide Site–Specific Antibodies," *Meth. Enzymol.* 178:739–746 (1989).

Rosenthal, N., "Identification of Regulatory Elements of Cloned Genes with Functional Assays," *Meth. Enzymol.* 152:704–720 (1987).

Sanger, F. et al., "DNA Sequencing with Chain–Terminating Inhibitors," *PNAS (USA)* 74:5463–5467 (1977).

Shih, E. et al., "An Adenoviral Vector System for Functional Identification of Nuclear Receptor Ligands," *Mol. Endocrinol.* 5:300–309 (1991).

Siegenthaler, G. et al., "Plasma and Skin Carriers for Natural and Synthetic Retinoids," *Arch. Dermatol.* 123:1690a–1692a (1987).

Siegenthaler, G. et al., "Terminal Differentiation in Cultured Human Keratinocytes is Associated with Increased Levels of Cellular Retinoic Acid–Binding Protein," *Exp. Cell Res.* 178:114–126 (1988).

Siegenthaler, G. et al., "Cellular Retinoic Acid–but Not Cellular Retinol–Binding Protein Is Elevated in Psioratic Plaques," *J. Invest. Dermatol.* 86:42–45 (1986).

Smith, W.C. et al., "A Retinoic Acid Response Element is Present in the Mouse Cellular Retinol Binding Protein I (mCRABPI) Promoter," *EMBO J.* 10:2223–2230 (1991).

Sporn, M.B. et al., "Role of Retinoids in Differentiation and Carcinogenesis," *Cancer Res.* 43:3034–3040 (1983).

Stoner, C.M. et al., "Mouse Cellular Retinoic Acid Binding Protein: Cloning,—Complementary DNA Sequence, and Messenger RNA Expression during the Retinoic Acid induced Differentiation of F9 Wild Type and RA–3–10 Mutant Teratocarcinoma Cells," *Cancer Res.* 49:1497–1504 (1989).

Summerbell, D. et al., "Retinoic acid, a Developmental Signalling Molecule," *Trends Neurosci.* 13:142–147 (1990).

Sundelin, J. et al., "The Primary Structure of Rat Liver Cellular Retinol–binding Protein," *J. Biol. Chem.* 260:6488–6493 (1985).

Takase, S. et al., "Transfer of Retinoic Acid from Its Complex with Cellular Retinoic Acid–Binding Protein to the Nucleus," *Arch. Biochem. Biophys.* 247:328–334 (1986).

Thompson, C.B. et al., "Levels of c–myc Oncogene mRNA are Invariant Throughout the Cell Cycle," *Nature* 314:363–366 (1985).

Umesono, K et al., "Direct Repeats as Selective Response Elements for the Thyroid Hormone, Retinoic Acid, and Vitamin $D_3$ Receptors," *Cell* 65:1255–1266 (1991).

Voorhees, J.J. et al., "Decreased Cyclic AMP in the Epidermis of Lesions of Psoriasis," *Arch. Dermatol.* 105:695–701 (1972).

Wei, L.N., et al., "Molecular Cloning and Transcriptional Mapping of the Mouse Cellular Retinoic Acid–Binding Protein Gene," *DNA Cell Biol.* 9:471–478 (1990).

Zelent, A. et al., "Cloning of Murine α and β Retinoic Acid Receptors and a Novel Receptor γ Predominantly Expressed in Skin," *Nature* 339:714–717 (1989).

```
Forward:  gaattctagaCTGCCCACCATGCCCCAACTTCGCCGGTACCTGGAAGATG
                                          T  C
                                                                        A
Reverse:  cactggatccAAGCTGGCCCACCTTTCACTCCCCGGACATAAATCCTCGTGCA
                                    T        A
```

FIG. 1A.

```
Forward primer:  5'-CAT CGG ATC CCA ACT GGA AGA TCA TCC GA-3'
                                     T   T       A
                                     A.
                                     G Reverse primer:  5'-CAT CGG ATC CCA ACG TCA TCT GCT GTC ATT-3'
                                     T   A   G  A              A
                                         C          C          C
                                         G          G          G
```

```
mCRABP-I    1   ----------A-T---MRS-----D-----A-----A-----H-----R-D---Q    50
hCRABP-I    1   ----------A-T---MRS-----D-----A-----A-----H-----R-D---Q    50
hCRABP-II   1   MPNFSGNWKIIRSENFEELLKVLGVNVMLRKIAVAAASKPAVEIKQEGDT          50
mCRABP-II   1   ---------------------------M-A-----M-M-----------N---       50 mCRABP-I    51  ------------------------------G-----E-----K-R--PT--N-----IH-T--T---  100
hCRABP-I    51  ------------------------------G-----E-----K-R--AT--N-----IH-T--T---  100
hCRABP-II   51  FYIKTSTTVRTTEINFKVGEEFEEQTVDGRPCKSLVKWESENKMVCEQKL                    100
mCRABP-II   51  ------------------I-------------------------G---------R----          100 mCRABP-I    101 -E-D-----Y-----A---*-----FG------------I-----         137
hCRABP-I    101 -E-D-----Y-----A---*-----FG------------I-----         137
hCRABP-II   101 LKGEGPKTSWTRELTNDGELILTMTADDVVCTRVYVRE                 138
mCRABP-II   101 ----------------S-----------------------               138
```

Figure 2B

|  | 1 |  |  |  | 5 |  |  |  |  | 10 |  |  |  |  | 15 |  |  |  |  | 20 |  |  |  |  | 25 |  |
|---|---|---|---|---|---|---|---|---|---|---|---|---|---|---|---|---|---|---|---|---|---|---|---|---|---|---|
| hCRABP-I | M | P | N | F | A | G | T | W | K | M | R | S | S | E | N | F | D | E | L | L | K | A | L | G | V | N |
| mCRABP-I | M | P | N | F | A | G | T | W | K | M | R | S | S | E | N | F | D | E | L | L | K | A | L | G | V | N |
| rCRABP-I |   | P | N | F | A | G | T | W | K | M | R | S | S | E | N | F | D | E | L | L | K | A | L | G | V | N |
| cCRABP-I |   | P | N | F | A | G | T | W | K | M | R | S | S | E | N | F | D | E | L | L | K | A | L | G | V | N |

|  | 1 |  |  |  | 5 |  |  |  |  | 10 |  |  |  |  | 15 |  |  |  |  | 20 |  |  |  |  | 25 |  |
|---|---|---|---|---|---|---|---|---|---|---|---|---|---|---|---|---|---|---|---|---|---|---|---|---|---|---|
| hCRABP-II | M | P | N | F | S | G | N | W | K | I | I | R | S | E | N | F | E | E | L | L | K | V | L | G | V | N |
| mCRABP-II | M | P | N | F | S | G | N | W | K | I | I | R | S | E | N | F | E | E | L | M | L | K | A | L | G | V | N |
| rCRABP-II | M | T | N | F | L | E | N | W | K | I | X | M | R | S | E | N | F | E | E | M | L | K | A | L | G | V | N |
| cCRABP-II |   | P | N | F | S | G | N | W | K | I | I | R | S | E | N | F | E | E | L | L | K | A | L | G | V | N |

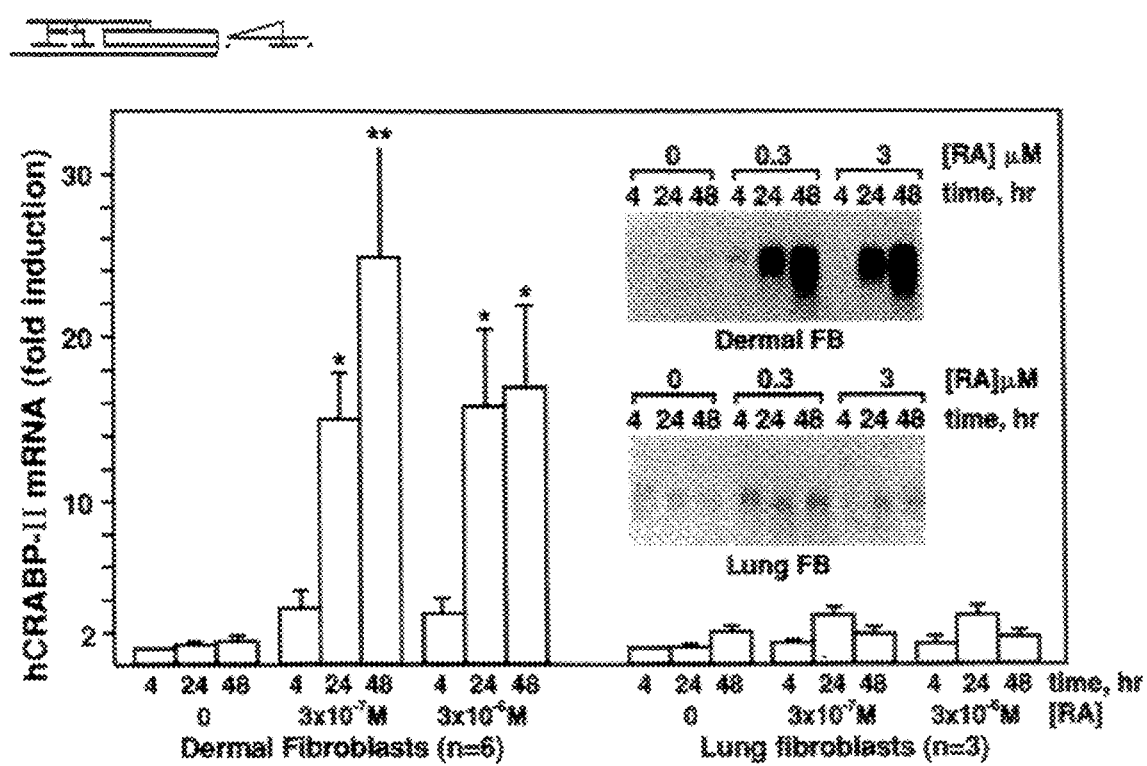

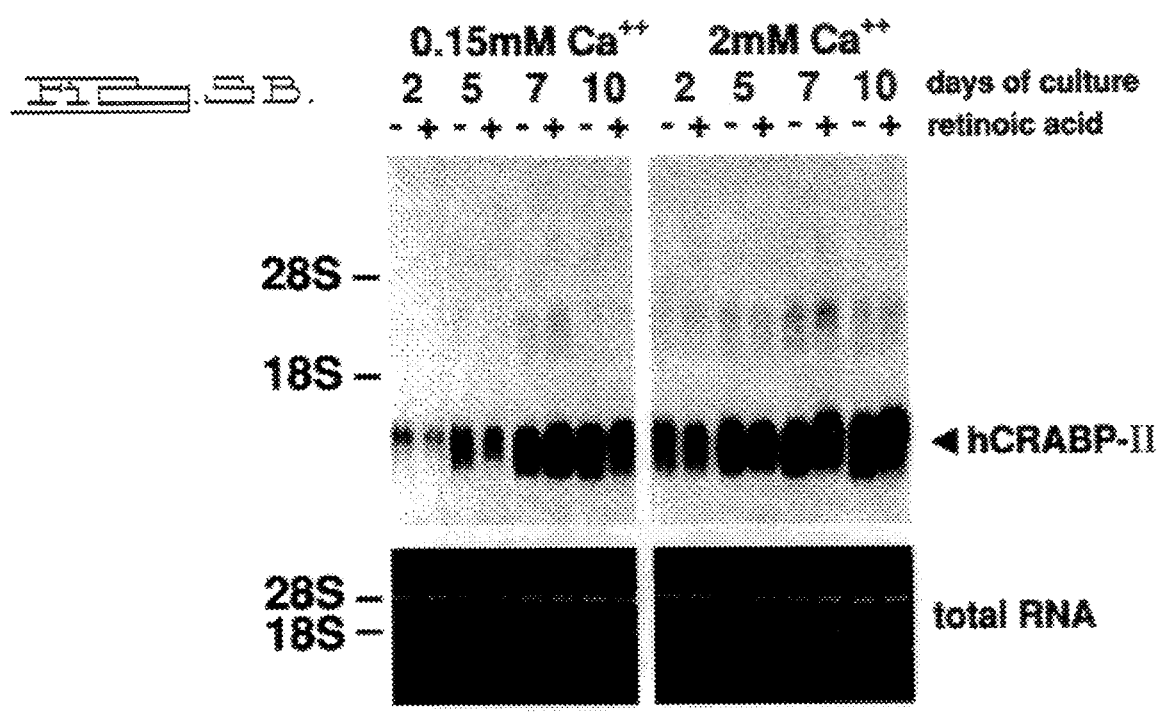

Figure 8A

```
-1038  CTGCAGGAAGCCGTGCCCTCCTCCCACCCTCTTTGATCTCCCGTTTCAAAGCCGCTCTCC  -979
- 978  AAGGGAGGGGAGGTCGCTCCTTCCGCCCGTTTTACAGCTCAGGATGGTGACACCTGAGAC  -919
- 918  CCTGCTCCGCCTTCTCCCCGGCACCCATCCTCCCGCCTATCTAGGTGGTGGCGCAGCTC   -859
- 858  GCCAGGGCTCCGCGCCTCTGTCCCCGCCTCCCTCCCTTCCCCCTACTGAGACCCCTCGGG -799
- 798  GTCTCGGGAGTGAAGCGACAGAGAAAGCGTTTTAATAAAGACCTTGCGTCAAGTGATTGG -739
- 738  CTGTGACCTCTGCCCTCCCAGCCTCGCGCCCTGGGCTCCTGCTTAACCCTTCAATGTCCG -670
                                                        AP2
- 678  CCCAGCGCATTAAGGGGAGCGAGTCGCCTGGCGACTACTTCCAGAGTCCCCAGGCATTAC -619
                                              Krox-24
- 618  GTGAGCCCGAAGCAGGGTGGAGGGGTGGGGGGACCGTGCCGCCCCCGCCCAGCCTCTCCG -559
- 558  AGTTGTTCCAGCAGGGGCGCCGTTGCCTCACTTAGATCCCTAACCCCCGGAACCCCGCA  -499
- 498  GCTCCCAAGCCCCTCTCTGAGTACGGAGTGGTCCCACTGGATCCAGTTCAGGGTTCAATG -439
                                        AP2
- 438  GAGCTAGGGCCAGCTACGGCTCAAGATCTGGGGTCCGCCTGCGGTGGGGTCGCCAGGTGT -379
- 378  CCGGCACCAAGGAGTTGAATGCACCGAGTCAGGTTGGGGATGGGTGGGGAACAGGCGAGA -319
- 318  CGTGAGGAACTCGGGTGGGGGACAGCCATACACGAGCCCTGAGCATCTGCGCCCGCAGCT -259
- 258  AGCTCCCCCCGCCTCTGCGGAGAGCGCGATTCAAGTGCTGGCTTTGCGTCCGCTTCCCCA -199
- 198  TCCACTTACTAGCGCAGGAGAAGGCTATCTCGGTCCCCAGAGAAGCCTGGACCCACACGC -139
              Krox-24                              Sp1
- 138  GGGCTAGATCCAGAGGTTGGTGGCGGGGGCGCAGGGCCCCAGGTGGGGGGGGCGGAGCG  - 79
- 78   GGAGGCGGGGCCACTTCAATCCTGGGCAGGGGCGGTTCCGTACAGGGTATAAAAGCTGTC - 19
                                                 +1
- 18   CGCGCGGGAGCCCAGGCCAGCTTTGGGGTTGTCCCTGGACTTGTCTTGGTTCCAGAACCT   42
  43   GACGACCCGGCGACGGCGACGTCTCTTTTGACTAAAAGACAGTGTCCAGTGCTCCAGCCT  102
                                     1
                                     MetProAsnPheSerGlyAsnTrpL
 103   AGGAGTCTACGGGGACCGCCTCCCGCGCCGCCACCATGCCCAACTTCTCTGGCAACTGGA  162
                                                              24
       ysIleIleArgSerGluAsnPheGluGluLeuLeuLysValLeuG
 163   AAATCATCCGATCGGAAAACTTCGAGGAATTGCTCAAAGTGCTGGtaaggaaatgttcg   222
 223   agggcccaggtgggcaaggggggctctggagtcctcgaagttggggatgagaaagaca   282
 283   gc.... 4kb ....cgcctaccgtctccttcaaggcactttcttagacacccgggcacc
       aggcagatgcaccccccaacacacccaccccaagcaagtcacaaatcagcctgctccaac
       tgtcttatggggagggtgtgagagaggtgcccaaaggcccctaaaaggtgagcctctcct
```

Figure 8B

```
                 25
           lyValAsnValMetLeuArgLysIleAlaValAlaAlaAlaSerLysP
ctctccccacagGGGTGAATGTGATGCTGAGGAAGATTGCTGTGGCTGCAGCGTCCAAGC roAlaValGluIleLysGlnGluGlyAspThrPheTyrIleLysThrSerThrThrValA
CAGCAGTGGAGATCAAACAGGAGGGAGACACTTTCTACATCAAAACCTCCACCACCGTGC rgThrThrGluIleAsnPheLysValGlyGluGluPheGluGluGlnThrValAspGlyA
GCACCACAGAGATTAACTTCAAGGTTGGGGAGGAGTTTGAGGAGCAGACTGTGGATGGA
     83
rgProCysLys
GGCCCTGTAAGgtgagtgccagaaggggctccagggtcatggcgtcattgccctgcctct caacctgccattttccaggctagcagttaactcctagcttctctctgtcccagtagggaa aatccctaggtagtggtgggggctagaaaggggctctctcccttatccctctcactgcat
                                       84
                                         SerLeuValLysTr
tgcccctgctatgggcccagctcacttggccacctgtctcttgcagAGCCTGGTGAAATG pGluSerGluAsnLysMetValCysGluGlnLysLeuLeuLysGlyGluGlyProLysTh
GGAGAGTGAGAATAAAATGGTCTGTGAGCAGAAGCTCCTGAAGGGAGAGGGCCCCAAGAC
                                          122
rSerTrpThrArgGluLeuThrAsnAspGlyGluLeuIleLeu
CTCGTGGACCAGAGAACTGACCAACGATGGGAACTGATCCTGgtaagtcctgcctcctc cccactaatagcaaacccagtgctaccttccaagattctctgggagacccagggtgcag gagactcaagaacaaccatggctggactccgcaccctgctgatgggactgcttgaacaga actaaggtgtccctatcccatacagtgccctgtgtgaattagaaatggtgttccttttat gcaagcaaagggcatgtactgagggatcccagcagttcttcagggagatcttcctggctt gaggaggaggacgggccccagggctctattgctatcctccctccattgatgcctgggcat tctgggaccagctcctgcctgttggtcttgagccaagaagcaggtttggacctggaggcc aagcagagtacctccattcaaccctcctctccaaagccacaggaccccaggggcctctca
                  123
                    ThrMetThrAlaAspAspValValCysThrArg
ggctaacaactacttctgtccttccagACCATGACGGCGGATGACGTTGTGTGCACCAGG
              138
ValTyrValArgGlu***
GTCTACGTCCGAGAGTGAGTGGCCACAGGTAGAACCGCGGCCGAAGCCCACCACTGGCCA

TGCTCACCGCCCTGCTTCACTGCCCCCTCCGTCCCACCCCCTCCTTCTAGGATAGCGCTC

CCCTTACCCCAGTCACTTCTGGGGGTCACTGGGATGCCTCTTGCAGGGTCTTGCTTTCTT

TGACCTCTTCTCTCCTCCCCTACACCAACAAAGAGGAATGGCTGCAAGAGCCCAGATCAC

CCATTCCGGGTTCACTCCCCGCCTCCCCAAGTCAGCAGTCCTAGCCCCAAACCAGCCCAG

AGCAGGGTCTCTCTAAAGGGGACTTGAGGGCCTGAGCAGGAAAGACTGGCCCTCTAGCTT

CTACCCTTTGTCCCTGTAGCCTATACAGTTTAGAATATTTATTTGTTAATTTTATTAAAA

TGCTTTAAAAAAATAAAACCTGTCTCTGGCTCATTGGGCAGGTAGATAAGTCACCTGAGT
```

HUMAN CRABP-I AND CRABP-II

RELATED APPLICATIONS

This is a divisional of U.S. patent application Ser. No. 08/241,664, filed May 11, 1994, entitled "HUMAN CRABP-I AND CRABP-II," which is a continuation of U.S. patent application Ser. No. 07/874,847, filed Apr. 28, 1992, entitled "HUMAN CRABP-I AND CRABP-II", now abandoned, which is a continuation-in-part of U.S. Ser. No. 07/751,893, filed Aug. 30, 1991, entitled "Human CRABP-I and CRABP-II," now abandoned.

FIELD OF THE INVENTION

The present invention relates generally to cellular retinoic acid binding proteins (CRABPs) and, more specifically, to human CRABP-I and CRABP-II and the sequences encoding them and their use in various assay systems for screening and diagnostic applications and for therapeutic purposes.

GENBANK ACCESSION INFORMATION

| GENE | ACCESSION NO. |
| --- | --- |
| human CRABP-II | M68867 |

BACKGROUND OF THE INVENTION

Retinoids are essential regulators of epithelial cell growth and cellular differentiation, skin being a major target in both normal and pathological states. Sporn, M. B. et al., Cancer Res. 43:3034–3040 (1983); Kopan, R. et al., J. Cell Biol. 109:295–307 (1989); Asselineau, D. et al., Dev. Biol. 133:322–335 (1989); and Lippman, S. M. et al., Pharmacol. Ther. 40:107–122 (1989). It has been shown that retinoids prevent cancer in skin and have efficacy as agents in human malignant and premalignant cutaneous disorders. Asselineau, D. et al., Dev. Biol. 133:322–335 (1989). It has also been shown that retinoids cause growth inhibition in many hyper-proliferating cell lines, a feature that makes the compounds of fundamental interest as anti-tumor and anti-psoriatic agents. Sporn, M. B. et al., Cancer Res. 43:3034–3040 (1983); and Asselineau, D. et al., Dev. Biol. 133:322–335 (1989). Retinoids also play fundamental roles in directing the spatial organization of cells during development and the generation of vertebrate limbs. Eichele, G. Trends Genet. 5:246–251 (1989); and Summerbell, D. et al., Trends Neurosci. 13:142–147 (1990).

The elucidation of the function of retinoids in the complex biological processes involved in cell growth and differentiation requires the identification of the specific components of the retinoid signal transduction system as well as the genes directly regulated by this system. Several intracellular retinoid-binding proteins have already been identified, including cellular retinol-binding proteins (CRBP), nuclear retinoic acid receptors (RAR), cellular retinoic acid binding proteins (CRABP) and, most recently, RXRs, also belonging to the nuclear receptor superfamily of genes. See Sundelin, J. et al., J. Biol. Chem. 260:6488–6493 (1985); Li, E. et al., PNAS (USA) 83:5779–5783 (1986); Nilsson, M. H. L. et al., Eur. J. Biochem. 173:45–51 (1988); Stoner, C. M. et al., Cancer Res. 49:1497–1504 (1989); Giguere, V. et al., PNAS (USA) 87:6233–6237 (1990); Petkovich, M. et al., Nature 330:444–450 (1987); Brand, N. et al., Nature 332:850–853 (1988); Benbrook, D. et al., Nature 333:669–672 (1988); Zelent, A. et al., Nature 339:714–717 (1989); Krust, A. et al., PNAS (USA) 86:5310–5314 (1989); and Mangelsdorf, D. J. et al., Nature 345:224–229 (1990).

Cellular retinoic acid binding proteins (CRABP) are low molecular weight proteins present in human skin with increased levels found in psoriatic lesions and after external and systemic retinoid treatment. Siegenthaler, G. et al., J. Invest. Dermatol. 86:42–45 (1986); Hirschel-Scholz, S. et al., Eur. J. Clin. Invest. 19:220–227 (1989); and Siegenthaler, G. et al., Arch. Dermatol. 123:1690–1692 (1987). Although undetectable in keratinocytes grown in low calcium medium, CRABP is expressed when a more differentiated phenotype is induced by growth to confluence in the presence of elevated extracellular calcium concentrations. Siegenthaler, G. et al., Exp. Cell Res. 178:114–126 (1988).

Although the precise role of CRABP in retinoic acid (RA) action has not been determined, it has been suggested that CRABP might act as a shuttle protein, facilitating the movement of RA to the nucleus, or that CRABP might sequester RA, thereby decreasing the cellular response. Takase, S. et al., Arch. Biochem. Biophys. 247:328–334 (1986); Maden, M. et al., Nature 335:733–735 (1988). In a recent study, it was found that all biologically active RA analogs in F9 cells bound to RARs, while two of them did not bind to CRABP. Benbrook, D. et al., Nature 333:669–672 (1988). This suggests that retinoid binding to RA, but not necessarily to CRABP is necessary to induce cell differentiation.

The effects of retinoic acid on gene transcription can be mediated by retinoic acid receptors (RARs) and retinoid X receptors (RXRs). Leed, M. et al., Cell 53:377–395 (1992); Mangelsdorf, D. J. et al., Genes Dev. 6:329–344 (1992). RARs have been shown to bind retinoic acid (RA) with high affinity, while RXRs apparently have no affinity for this ligand. Mangelsdorf, D. J. et al., Nature 345:224–229 (1990). However, it was recently demonstrated that 9-cis RA can bind to RXR - $\alpha$ with high affinity. Levin, A. A. et al., Nature 355:359–361 (1992); Heyman, R. A. et al., Cell 68:397–406 (1992). CRABPs have been shown to bind RA with high affinity, but their function is poorly understood. However, it was recently demonstrated that CRABP may be involved in cytochrome P-450 metabolism of RA. Fiorella, P. D. et al., J. Biol. Chem. 268:16572–16579 (1991).

Two isoforms of CRABP, CRABP-I and II, have been identified and cloned in the mouse. Stoner, C. M. et al., Cancer Res. 49:1497–1504 (1989); Giguere, V. et al., PNAS (USA) 87:6233–6237 (1990); Nilsson, M. H. L et al., Eur. J. Biochem. 173:45–51 (1988). By isoform is meant two amino acid sequences with substantial sequence identity. Bovine CRABP-I has also been sequenced, and the $NH_2$ terminal regions of rat and chicken CRABP-I have also been recently determined. Bailey, J. S. et al., J. Biol. Chem. 263:9326–9332 (1988); Kitamoto, J. et al., Biochem. Biophys. Res. Comm. 157:1302–1308 (1988). Human CRABP has, however, not been previously isolated or cloned.

SUMMARY OF THE INVENTION

The sequences encoding two isoforms of human cellular retinoic acid binding proteins, designated CRABP-I and CRABP-II, and the gene for CRABP-II, have been cloned and sequenced. Their nucleic acid and corresponding amino acid sequences are set forth in the sequence listing (SEQ ID NOS:1–6) preceding the claims. Expression of human CRABP-II, but not CRABP-I was markedly increased in human skin in vivo and in skin fibroblasts in vitro after treatment with retinoic acid (RA) and after treatments which induce keratinocyte differentiation. The importance of RA dependent mRNA stabilization for keying CRABP II message at induced levels once transcription has occurred is also described.

The cloning and sequencing of human CRABP provides the basis for the construction of human CRABP-I and II viral, prokaryotic and eukaryotic expression vectors and recombinant expression constructs. Human CRABP can now also be produced synthetically or ex vivo (outside the human body), for example, through the production of fusion proteins in bacteria and later cleavage and purification of CRABP therefrom.

Ligand binding studies utilizing human CRABP sequences can determine ligand binding affinity and the interaction of human CRABP with other human retinoid-binding proteins, and can be used to better identify tissue-specific drugs for pathologies in which retinoids are implicated. Various assay schemes, including reporter assay systems, direct and competition hybridization and binding assays employ the nucleic and amino acid sequences herein described. Antibodies or binding fragments thereof produced to human CRABP can also be used in immunoassays of patient tissues for CRABP levels for diagnosis and the monitoring of treatment. Purified or synthetic human CRABP can also be used for supplementation therapy.

Other features and advantages of the present invention will become apparent from the following description and appended claims, taken in conjunction with the accompanying drawings.

BRIEF DESCRIPTION OF THE DRAWINGS

FIGS. 1A–1B gives the sequences of the forward and reverse degenerate primers used in cloning human CRABP (SEQ ID NOS:7–10).

FIGS. 2A–2B compares human, mouse, rat and chicken CRABP (SEQ ID NOS:11–16). Panel A is a comparison of the amino acid sequences of human (h) CRABP-I (SEQ ID NO:4), human (h) CRABP-II (SEQ ID NO:2), mouse (m) CRABP, (SEQ ID NO:11) and mouse (m) CRABP-II (SEQ ID NO:12). Dashes represent sequence identity; the asterisk at residue 118 represents a gap introduced in the CRABP-I sequence for maximum alignment. Panel B is a sequence comparison of the $NH_2$-terminal ends of the CRABP-I of human (h) (the last 26 amino acids of SEQ ID NO:4), mouse (m) (the last 26 amino acids of SEQ ID NO:11), rat (r) (SEQ ID NO:15) and chicken (c) (SEQ ID NO:13) and the CRABP-II of human (h) (last 26 amino acids of SEQ ID NO:2), mouse (m) (last 26 amino acids of SEQ ID NO:12) rat (r) (SEQ ID NO:14) and chicken (c) (SEQ ID NO:16). Boxed residues represent those dissimilar to human CRABP-II.

FIG. 4 is a bar graph of the RNA blot hybridization results (quantitated by laser densitometry) of nine independent experiments involving five dermal fibroblast lines prepared from three individuals and three diploid human lung fibroblast lines. The results illustrate the induction of human CRABP-II mRNA in human dermal fibroblasts compared to lung fibroblasts. The Inset shows the relevant autoradiographic bands from two representative experiments comparing dermal and lung fibroblasts.

FIGS. 5A, 5B and 5C illustrate the expression of CRABP-II mRNA in cultured keratinocytes under various conditions. FIG. 5A is a bar graph of the results obtained for seven independent keratinocyte strains and illustrates the effects of confluence on human CRABP-II mRNA levels. The error bars represent±SE p<0.005, *p<0.0005 relative to cells 2 days preconfluence. FIG. 5B shows the effects of RA and increased calcium concentration on human CRABP-II mRNA levels in postconfluent keratinocytes, with treatment for prolonged periods with low concentrations of RA ($3\times10^{-9}$M) having no detectable effect. FIG. 5C illustrates that prolonged treatment of postconfluent keratinocytes with higher concentrations of RA ($3-10^{-6}$M) reduced CRABP-II mRNA to undetectable levels.

FIG. 8 illustrates the nucleotide sequence and shown above the nucleotide sequence is the deduced amino acid sequence (SEQ ID NO:2) of the human CRABP-II gene.

DETAILED DESCRIPTION OF THE PREFERRED EMBODIMENTS

OVERVIEW

Figure 3:
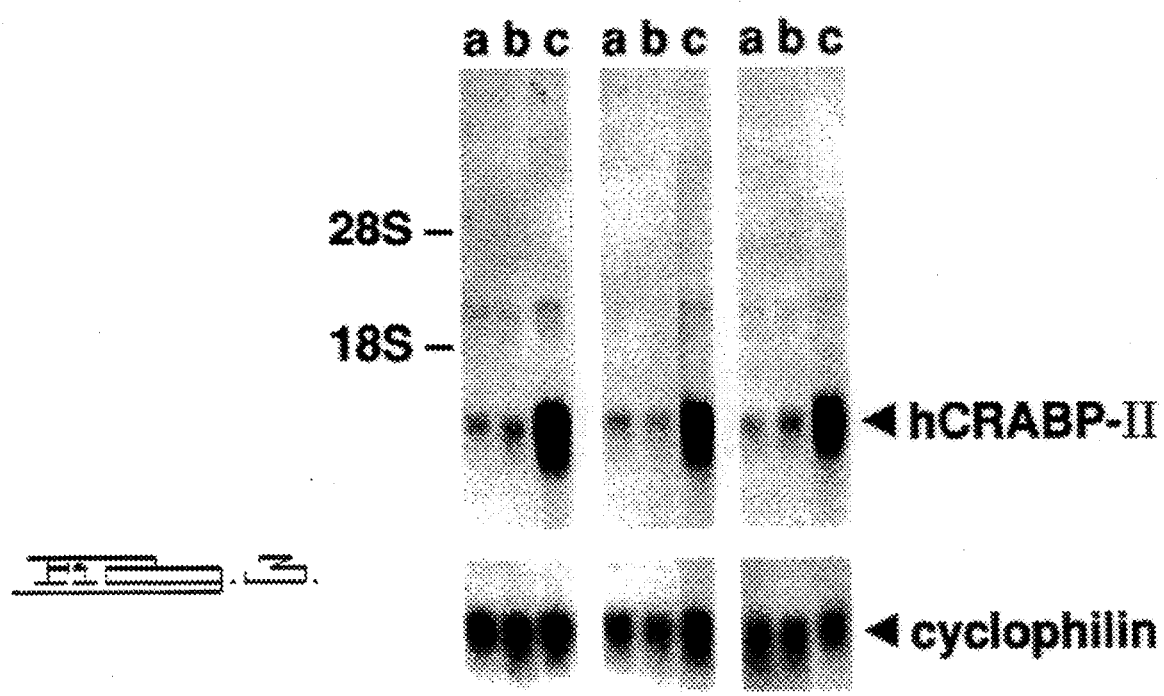
FIG. 3 is an autoradiogram of RNA blots derived from three individuals which illustrates induction of CRABP-II mRNA in human skin by topically applied retinoic acid (RA). Lane (a) represents no treatments; lane (b) RA vehicle; and lane (c) 0.1% RA cream in RA vehicle under occlusion.

The cloning and sequencing of two human CRABP cDNAs revealed one with a predicted amino acid sequence 99.3% identical to the mouse and bovine CRABP-I, and a second with a predicted amino acid sequence, 93.5% identical to the mouse CRABP-II. The CRABP-II described herein appears to be the human homolog to mouse CRABP-II, since both are expressed in adult skin, and is therefor designated as such. The high amino acid homology seen between bovine, mouse and human CRABP-I indicates that this isoform has been more conserved throughout evolution than the CRABP-II (FIG. 2A described below). This was especially evident when the $NH_2$-terminal sequence between rat, chicken, mouse and human CRABP-I and CRABP-II were compared. No differences were seen between the CRABP-Is, while several differences exist between the CRABP-IIs.

CRABP-I transcripts were undetectable in adult human epidermis by RNA blot hybridization, while the CRABP-II cDNA probe detected an approximately 1.2 kilobase (kb) mRNA transcript. External application of 0.1% retinoic acid cream in vivo for 16 hours resulted in a 16-fold induction of CRABP-II, but not CRABP-I. CRABP-II mRNA, was also markedly increased (>15-fold) by retinoic acid treatment of fibroblast cultured from human skin, whereas no significant induction of CRABP-II mRNA was observed in human lung fibroblast. Human CRABP-II, but not CRABP-I mRNA was significantly Induced by treatments which induce keratinocyte differentiation in vitro. Highly Increased levels of CRABP-II RNA were found in psoriatic epidermis when compared to normal epidermis for 10 different patients. CRABP-I message levels were on the other hand very low or undetectable in both normal and psoriatic skin (data not presented in Figures). Previous studies of the induction of CRABP by natural and synthetic retinoids and their Increased levels during keratinocyte differentiation are consistent with the expression of CRABP-II message seen in the present investigation, but not with the expression of CRABP-I. These studies thus identify CRABP-II as the isoform likely to be expressed and regulated by RA in adult human skin.

Since mRNA isolated from skin biopsies used in this study is approximately 95% derived from keratinocytes (see Voorhees, J. J. et al., *Arch. Dermatol.* 105:695–701 (1972)), the majority of RA induction of CRABP-II seen in vivo (FIG. 3 described below) cannot be explained by the presence of mRNA derived from dermal fibroblasts. This is In contrast to the reduction of CRABP-II transcripts observed in response to high concentrations of RA in keratinocytes in vitro (FIG. 5C described below). When grown to postconfluence under the same conditions used herein, human keratinocytes undergo coordinate increases in involucrin content and transglutaminase activity, two key determinants of cornified envelope formation during terminal differentiation. Pillai, S. et al., *J. Cell Physiol.* 143:294–302 (1990). Moreover, these events are accelerated and began to occur prior to confluence when the extracellular calcium concentrations were increased to 1.2 or 2.4 mM. Pillai, S. et al., *J. Cell. Physiol.* 143:294–302 (1990). CRABP-II mRNA levels responded to confluence and external calcium in an identical fashion (FIG. 5 described below). These results strongly favor the concept that the stratified structure of the epidermis and/or the presence of dermis is an important determinant of CRABP-II regulation in vivo, and may help to account for the differential responsiveness of keratinocytes to RA in vitro and in vivo. The negative effect of high concentrations of RA on CRABP-II expression seen in vitro is similar to the effect of this compound on transglutaminase type I mRNA levels in cultured keratinocytes. See Floyd, E. E. et al., Mol. Cell. Biol. 9:4846–4851 (1989).

Whether RA induction of the human CRABP-II gene occurs at the level of transcription and whether this regulation is mediated by specific nuclear receptors remains to be investigated. It has been shown that human skin as well as cultured human skin fibroblasts express RAR-$\gamma$. Krust, A. et al., PNAS (USA). 86:5310–5314 (1989); and Elder, J. T. et al., *J. Invest. Dermatol.* 96:425–433 (1991 ). However, this does not explain the lack of RA induction of CRABP-II mRNA seen in cultured human lung fibroblasts and keratinocytes, also known to express RAR-$\gamma$. Elder, J. T. et al., *J. Invest. Dermatol.* 96:425–433 (1991). If the CRABP-II gene is regulated by the RARs, additional tissue or cell-specific factors may be required for RA induction.

Members of the nuclear superfamily of receptors have been shown to interact with their responsive elements as dimers. Glass, C. K. et al., *Cell* 59:697–708 (1989). RARs have also been shown to interact with other members of this family (i.e., the thyroid hormone receptors) forming heterodimers. Glass, C. K. et al., *Cell* 59:697–708 (1989). One of the most exciting findings recently is that the thyroid hormone receptors require an auxiliary protein (TRAP) to interact with the thyroid hormone responsive element in the growth hormone gene. O'Donell, A. L. et al., *Mol. Endocrinol.* 5:94–99 (1991). TRAP apparently is forming a heterodimer with the thyroid hormone receptor on the responsive element. Such dimerization between nuclear receptors and other transcription factors could explain tissue-specific regulation. If there is a skin-specific factor forming a heterodimer with the RARs, that could explain why the CRABP-II gene is induced by RA in skin fibroblasts, but not lung fibroblasts.

In summary, we have demonstrated that CRABP-II is expressed in human skin in vivo and the CRABP-II gene appears regulated by RA in skin in vivo and in cultured skin fibroblasts in vitro. CRABP-II was not, however, induced by RA in cultured lung fibroblasts, demonstrating cell-specific regulation of this gene. CRABP-I, on the other hand, does not appear regulated by RA and is found at very low or undetectable levels in human skin in vivo, as well as in keratinocytes and fibroblasts. This suggests that CRABP-II may participate in a regulatory feedback mechanism to control the action of RA on cell differentiation in skin. The identification of human CRABPs, RARs and RXRs now allows studies, such as those described below, on interactions between members of these families in the complex molecular and cellular mechanisms of RA action.

The identification of the nucleic and amino acids sequences of human CRABP-I and CRABP-II provide the basis for a variety of recombinant products, including vectors carrying the human CRABP cDNA sequences and expression constructs cotransfected or infected with such vectors. For example, plasmid or viral vectors carrying human CRABP cDNA have been constructed and are used to cotransfect or coinfect receptor-deficient CV-1 monkey kidney cells. Reporter assay systems utilizing CV-1 recombinant expression constructs which include human CRABP cDNA, a reporter element containing a retinoid responsive element and a reporter gene, and preferably internal control sequences, such as generally described in Aström, A. et al., *Biochem. Biophys. Res. Comm.* 173:339–345 (1990), can also now be constructed. Chimeric receptor proteins such as those described in U.S. Pat. No. 4,981,734 to Evans et al., can also be synthesized and utilized in reporter assays.

Figure 6:
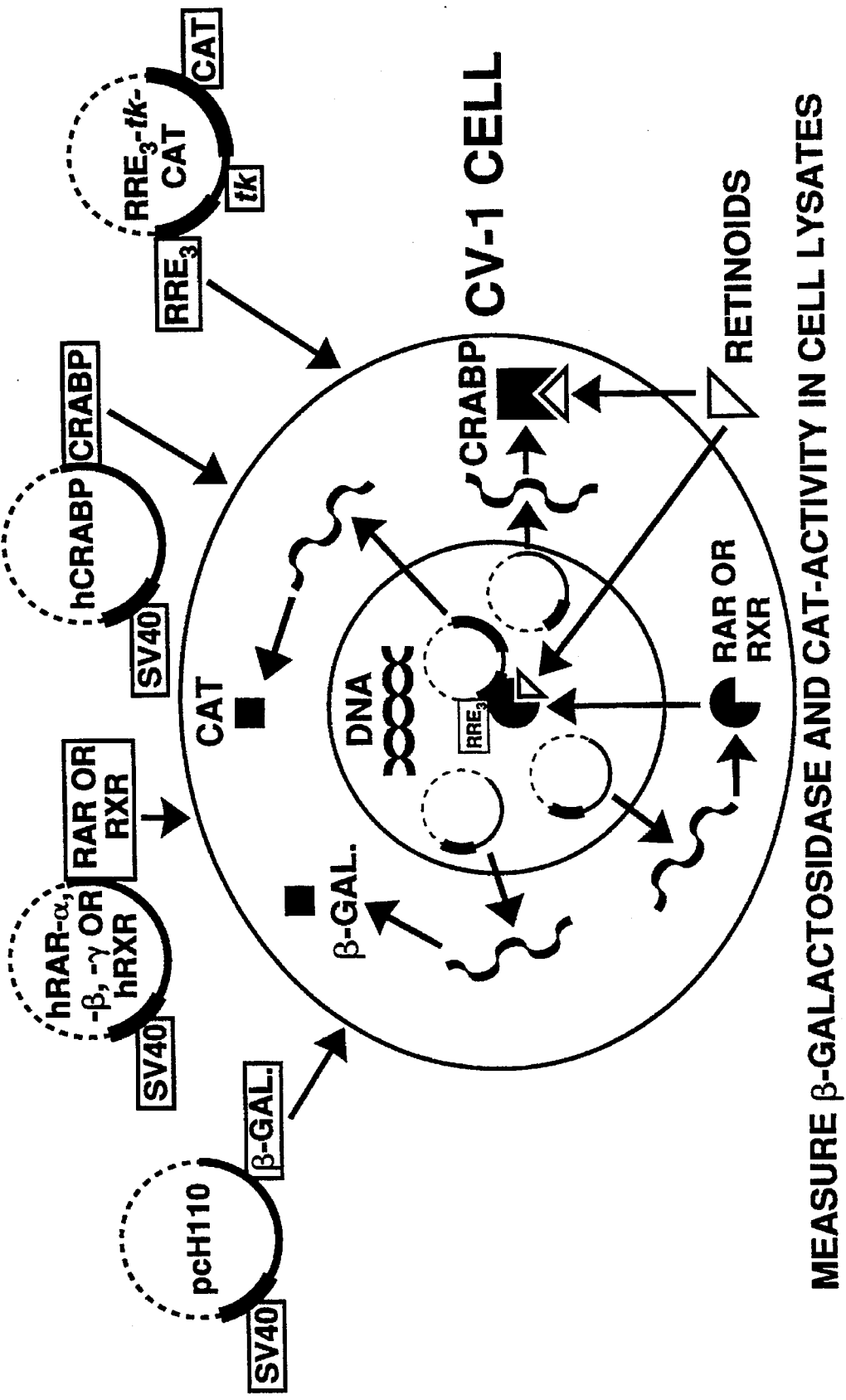
FIG. 6 is a schematic diagram of a retinoic acid receptor (RAR)-CRABP or RXR-CRABP cotransfection assay.

Assay systems employing human CRABP in conjunction with additional retinoid-binding proteins are also contemplated as within the scope of the Invention. For example, as shown schematically in FIG. 6, viral (e.g. SV40) vector carrying a human CRABP, a reporter plasmid carrying the retinoid responsive element (e.g. RRE$_3$-tk-CAT), a viral (e.g. SV40) vector carrying a human RAR or RXR of interest and a $\beta$-galactosidase vector (pcH110) for an internal control are coinfected or cotransfected into CV-1 cells. As shown in FIG. 6, the recombinant CV-1 construct is exposed to the binding ligand (e.g. retinoid) of interest. By ligand is meant a molecule which binds to the receptor binding protein and induces the expression of the gene of interest. In this assay system, induction of the reporter gene is used to assay for ligand binding to receptor protein. Absent any additional regulatory requirements, functional ligand would bind RAR or RXR, stimulating the expression (and translation) of the reporter gene (CAT). By including human CRABP in the system, the interaction between human CRABP and RAR or RXR or other binding receptors can be determined. For example, if CRABP sequesters RA in the cytoplasm, less ligand will reach the nucleus, thereby reducing RAR or RXR-mediated stimulation of the reporter gene.

The sequencing of human CRABP also allows the raising or production of antibodies or binding fragments, e.g. F'(ab), which can be used in immunoassays to further characterize binding or for diagnostic purposes and to monitor the course of patient treatment. For example, patient tissue can be assayed for the presence and levels of human CRABP to diagnose particular conditions where retinoids are implicated and to monitor the effectiveness of drugs and other treatments in altering patient levels of CRABP. CRABP purified directly from human tissue or cells, in culture or human CRABP produced synthetically or ex vivo will also provide CRABP for supplementation therapy where needed.

The gene for human cellular retinoic acid-binding protein II (CRABP-II) has been cloned and sequenced. It was isolated from a human placenta genomic library and is contained within one bacteriophage clone. The gene spans 6 kilobases and consists of four exons and three introns as do other members of the hydrophobic ligand binding protein gene family. Wei, L. N. et al., DNA Cell Biol. 9:471-478 (1990). The mouse CRABP-I gene has previously been cloned, demonstrating a different intron, but similar exon arrangement. Wei, L. N. et al., DNA Cell Biol. 9:471-478 (1990). One major transcription site was mapped to an A residue 137 nucleotides upstream of the ATG initiation codon. The sequence of the upstream region of the CRABP-II gene is rather GC rich and has a TATA box at −31, and several possible binding sites for transcription factors.

Figure 10:
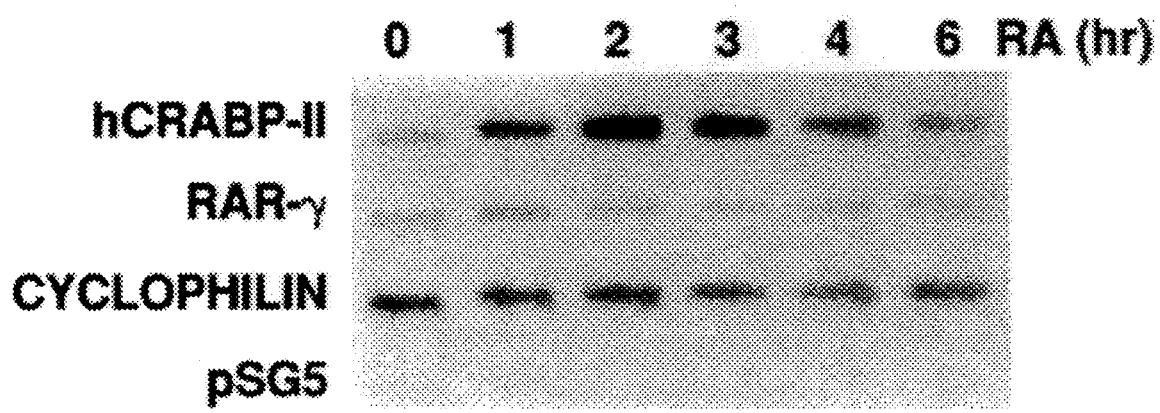
FIG. 10 illustrates a nuclear run-off assay using nuclei isolated from cultured human skin fibroblasts treated with retinoic acid.
Figure 11:
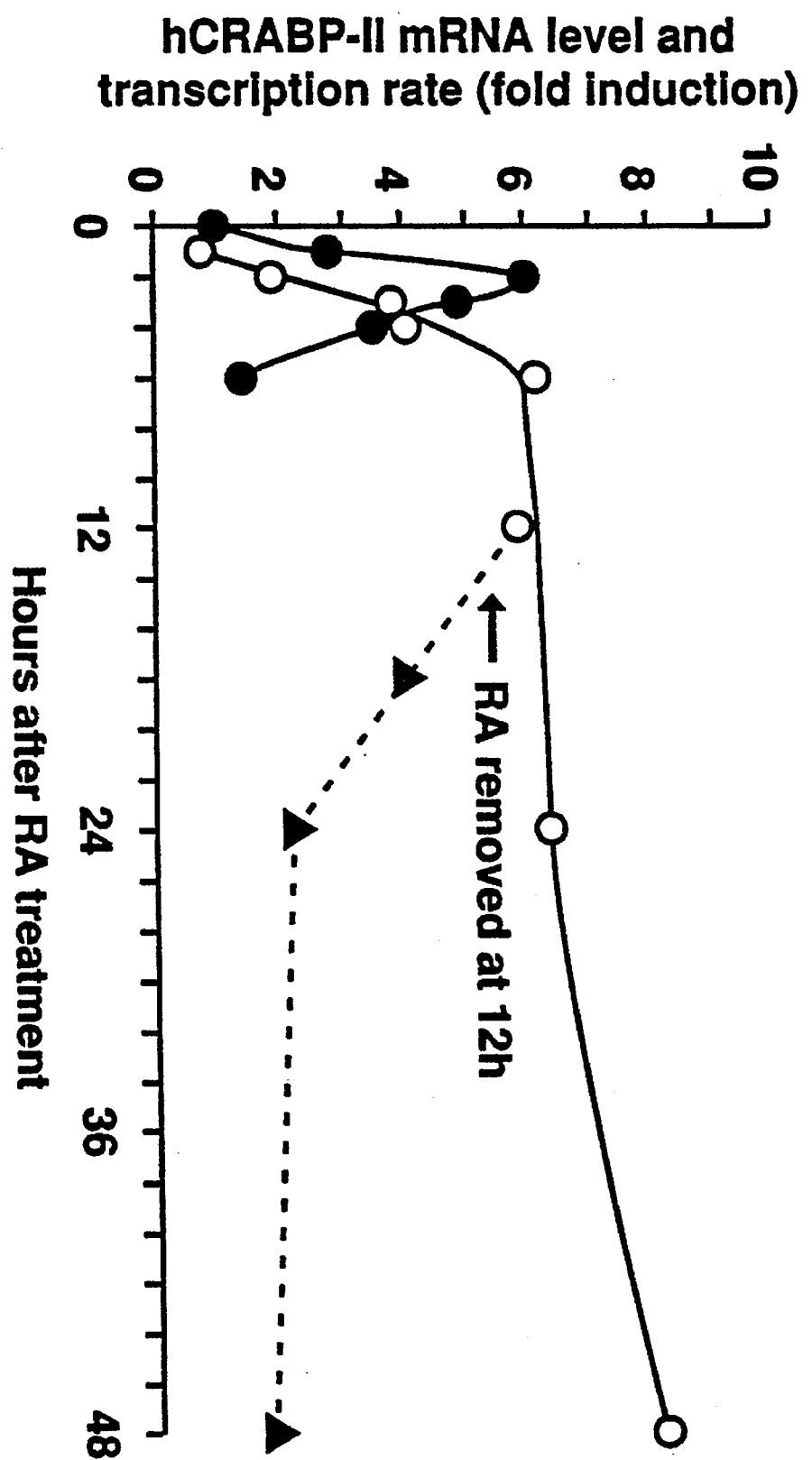
FIG. 11 illustrates the mRNA level and transcription rate of CRABP-II after quantitation by phosphorimaging and normalization to cyclophilin.
Figure 12:
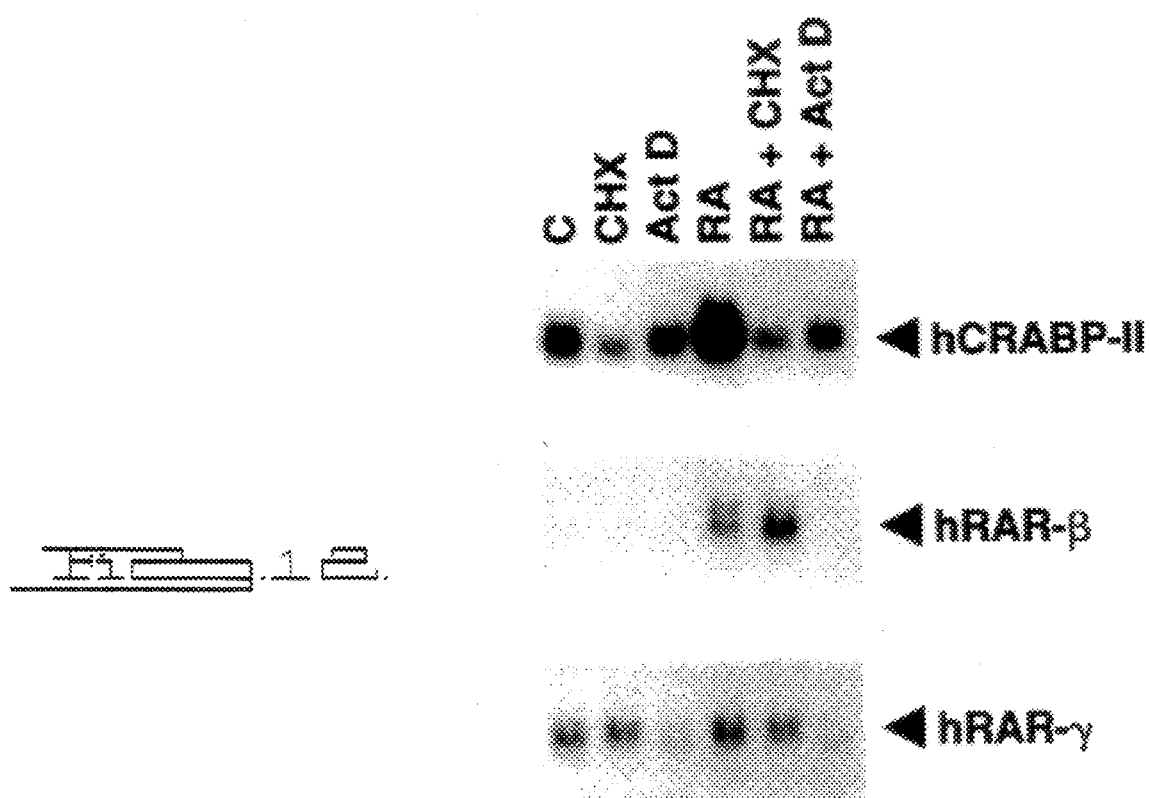
FIG. 12 is an autoradiogram demonstrating the effects of cycloheximide or actinomycin D on the induction of CRABP-II mRNA expression.
Figure 13:
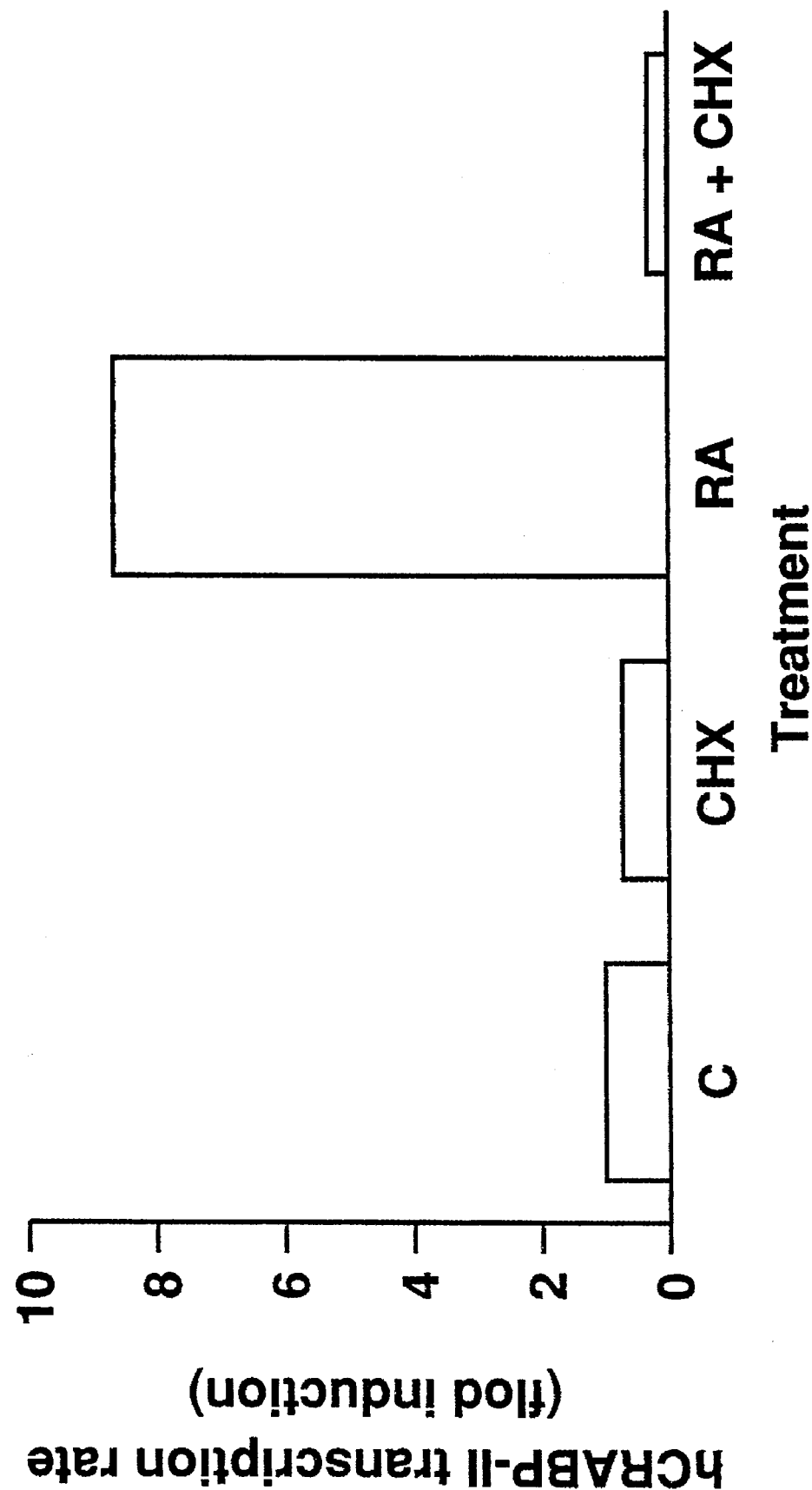
FIG. 13 is a bar graph demonstrating the effects of cycloheximide on CRABP-II transcription rates determined by nuclear run-on assays.

Of special interest is the presence of potential AP2 (CCSCRGGC) (see nucleotides 408 to 415 of SEQ ID NO:5) sites in the 5' flanking region. AP2 has been shown to be identical to the transcription factor KER1 which has been suggested to be generally involved in epidermal gene regulation. Leask, A. et al., PNAS (USA) 88:7948-7952 (1991). CRABP-II is predominantly expressed in the skin of adult mice and we have recently demonstrated that CRABP-II, but not CRABP-I is expressed in human skin. Giguere, V. et al., PNAS (USA) 87:6233-6237 (1990); Aström, A. et al., J. Biol. Chem. 266:17662-17666 (1991). In addition, both AP2 and CRABP-II mRNA have been shown to be induced by RA. Aström, A. et al., J. Biol. Chem. 266:17662-17666 (1991); Lüscher, B. et al., Genes Dev. 3:1507-1517 (1989). Whether AP2 is involved in skin-specific expression and RA induction of the CRABP-II gene remains to be determined. As shown in FIG. 8, the upstream region also contains a high affinity Sp1 binding site (GGGGCGGAGC) (see nucleotides 950 to 959 of SEQ ID NO:5) close to the TATA box, and two sequences (GCGGGGGCG) (see nucleotides 923 to 931 of SEQ ID NO:5) identical to Krox-24 binding sites. Kadonaga, J. T. et al., Trends Bichem. Sci. 11:20-23 (1986). Lemaire, P. et al., Mol. Cell. Biol. 10:3456-3467 (1990). Krox-24 is a member of the early responsive gene family, suggested to be Involved in regulation of cell proliferation and differentiation. Lemaire, P. et al., Mol. Cell. Biol. 10:34.56-3467 (1990); Edwards, S. A. et al., Dev. Biol. 148:165-173 (1991). It was recently shown that Egr-1 Krox-24 was induced by RA in embryonal P19 cells. The induction of Egr-1 protein by RA in these cells, demonstrated a transient-5 fold increase, peaking around 30-60 minutes and returned to basic levels between 60-90 minutes. Thus, as shown in FIG. 11, the induction of Egr-1 protein by RA just precedes CRABP-II gene transcription. However, the involvement of Egr-1 in RA induced transcriptional regulation of the CRABP-II gene in skin fibroblasts is unlikely, since Egr-1 was found to be induced by treatment of the cells with cycloheximide while CRABP-II gene expression in this study was found to be inhibited by this compound as demonstrated in FIGS. 12 and 13. Edwards, S. A. et al., Dev. Biol. 148:165-173 (1991). The upstream region of the CRABP-II gene also contains a direct repeat (G/AGTTCA) (see nucleotides 585 to 590 (R=A) and 592 to 597 (R=G) of SEQ ID NO:5) spaced with one nucleotide with homology to the RARE found in the RAR-$\beta_2$ promoter, except that the RAR-$\beta_2$ RARE is spaced by five nucleotides. Umesono, K. et al., Cell 65:1255-1266 (1991). it was recently shown that two other members of the hydrophobic ligand-binding family of genes contain a RARE (CRBP-I) and a RXRE (CRBP-II) in their promoters. Smith, W. C. et al., EMBO J. 10:2223-2230 (1991); Mangeisdorf, D. J. et al., Cell 66:555-561 (1991). Whether this direct repeat is functional remains to be determined. To determine whether RA induction of CRABP-II is transcriptional, nuclear run-on assays were performed. As can be seen in FIGS. 10 and 11, treatment of cultured human skin fibroblasts with RA resulted in a rapid transient 6-fold increase of transcription, followed by a 6-fold induction of CRABP-II mRNA levels. Thus, the CRABP-II gene is mainly transcriptionally activated by RA. The CRABP-II mRNA was rapidly induced within 2-6 hours in cultured human skin fibroblasts by retinoic acid, reaching a plateau after 6 hours of treatment. However, removal of retinoic acid from the medium after 12 hours caused a sharp decline in CRABP-II mRNA levels. The rapid increase of CRABP-II message was mainly due to an increased rate of transcription as determined by the nuclear run-on experiments as shown in FIG. 10. Increased transcription could be detected as early as 1 hour after addition of RA, peaked at 2 hours and returned to basal levels within 6 hours. In addition, both the accumulation of message, as shown in FIG. 12, and the induction of transcription, as shown in FIG. 13, by RA was Inhibited by cycloheximide, suggesting that the CRABP-II gene is transcriptionally regulated by a newly synthesized protein. Once transcription had occurred the message reached a plateau and did not decline until RA was removed from the medium. On-going protein synthesis was required for the transient increase in transcription, since the induction was blocked by cycloheximide. It is very unlikely that the decrease of CRABP-II mRNA seen was a result of reduced transcription of the gene, since the RA induction of transcription was transient and back to control levels within 6 hours. A more likely explanation would be that RA was Involved in stabilization of the CRABP-II message. The CRABP-II mRNA is likely to be unstable, since it contains AU rich sequences in the 3' untranslated region. Giguere, V. et al., PNAS (USA) 87:6233-6237 (1990); Aström, A. et al., J. Biol. Chem. 266:17662-17666 (1991). It has been shown that many transiently expressed genes, including lymphokine genes, c-myc, and c-los contain AU rich sequences in their 3' untranslated regions, and that the presence of these sequences correlates with rapid mRNA degradation. Cleveland, D. W. et al., New Biol. 1:121-126. Mechanisms by which CRABP-II mRNA stabilization could occur, may involve the production of a factor after treatment of the cells with RA, or interaction of RA with a preexisting factor, stabilizing the message. Since cycloheximide blocked the RA induced transcription of the gene and as a consequence, the induction of the message, the possibilities were not distinguishable. It has been demonstrated that the human CRABP-II gene is transiently transcriptionally induced by RA in human skin fibroblasts, and that this induction is dependent on on-going protein synthesis. The early induction of transcription is followed by a rapid increase in CRABP-II message levels that does not decrease until RA is removed from the medium, suggesting RA dependent mRNA stabilization.

It will be appreciated that the nucleotide and amino acid sequences of the present invention can include some variation from the sequences represented by and complementary to the sequences set forth in the Sequence Listing, but must be substantially represented by or complementary to those set forth therein. By "substantially represented by" or "substantially complementary to" is meant that any variation therein does not impair the functionality of the sequence to any significant degree. As used herein, A represents adenine; T represents thymine; G represents guanine; and C represents cytosine; except where otherwise indicated.

SPECIFIC EXAMPLES

SPECIFIC EXAMPLE 1. Cloning and Sequencing of Human CRABP

MATERIALS AND METHODS

Cloning of CRABP from human skin RNA by Polymerase Chain Reaction (PCR)

Total RNA was Isolated from human keratome biopsies as described in Elder, J. T. et al., *J. Invest. Dermatol.* 94:1925 (1990) and cDNA was synthesized by reverse transcription as described in Maniatis, T. et el., *Molecular Cloning: A Laboratory Manual, Cold Spring Harbor Laboratory*, Cold Spring Harbor, N.Y. (1982). Degenerate primers derived from mouse and bovine CRABP-I were designed so as to amplify the coding region. XbaI and BamHI sites were contained in the forward (SEQ ID NO:7) and reverse (SEQ ID NO:8) primers, respectively, which are shown in FIG. 1A.

The cDNA was used as a template for PCR (2 minutes denaturation at 92° C., 2 minutes, annealing at 42° C., 2 minutes amplification at 72° C. and final extension for 10 minutes). After 40 cycles, the length of the amplified DNA was determined on a 1.5% egarose gel. The amplified 436-bp region of CRABP was isolated from the gel, subcloned into Bluescript phagemid and sequenced as described below.

Screening and sequencing of cDNA clones

Poly A+ RNA was prepared from human skin as described in Elder, J. T. et al., *J. Invest. Dermatol.* 94:19–25 (1990) and used to prepare a cDNA library in Lambda ZapII (Stratagene Inc., La Jolla, Calif.). The library contained $1.0 \times 10^7$ primary recombinants. The 436-bp PCR product was labeled by random hexamer priming (Boeringer Mannheim, Indianapolis, Ind.) and used to screen the adult human whole skin cDNA library and a human skin fibroblast cDNA library in λgt11 (Clontech, Palo Alto, Calif.). Duplicate nitrocellulose filters were hybridized for 16 hours in 50% formamide containing 5×SSC (1×SSC=150 mM NaCl, 15 mM sodium citrate), 1×Denhardt's (0.02% Ficoll/0.02% bovine serum albumin/0.02% polyvinylpyrrolidone), 0.1% SDS (sodium dodecyl sulfate) and 200 μg/ml tRNA. The filters were washed two times for 20 minutes in 0.2×SSC, 0.2% SDS and one time for 20 minutes in 0.2×SSC, 0.1% SDS at 55° C. Two positive clones were isolated from the skin library and five clones from the skin fibroblast library. The clones from the skin library were rescued, while the clones from the fibroblast library were subcloned into Bluescript phagemids (Stratagene Inc., La Jolla, Calif.).

DNA sequence analysis was performed on both strands by dideoxy chain termination as generally described in Sanger, F. et al., *PNAS (USA)* 74:5463–5467 (1977), using modified T7 polymerase (Sequenase, U.S. Biochemical Corp.) and synthetic oligonucleotides.

Cell culture

Primary cultures of normal human keratinocytes were prepared as described in Boyce, S. T. et al., in *In Vitro Models for Cancer Research* (Weber, M. M., and Sekely, L. I., eds) Vol. 3, pp. 245–274. CRC Press, Boca Raton, Fla. (1986). Subcultures were expanded in keratinocyte growth medium (KGM) (Clonetics, San Diego, Calif.). Human dermal fibroblast cultures were prepared from punch biopsies of buttock skin (see Harper, R. A. et al., *Science* 204:526–527 (1979)) and propagated in modified McCoy's 5A medium containing 10% calf serum. Human lung fibroblasts were obtained from the American Type Culture Collection (ATCC) (Rockville, Md.) and grown in the same medium.

Northern analysis of mRNA

RNA was isolated from keratome biopsies and cultured cells by guanidinium isothiocyanate lysis and ultracentrifugation as previously described in Elder, J. T. et al., *J. Invest. Dermatol.* 94:19–25 (1990). For studies involving retinoic acid treatment, 0.1% RA cream (Retin-A, Ortho Pharmaceutical Corp. Raritan, N.J.) was applied once to skin and maintained under plastic wrap for 4 hours to 96 hours prior to biopsy. Adjacent sites were treated with Retin-A vehicle or left untreated. After 4 hours, 12 hours, 16 hours or 96 hours, keratome biopsies were obtained and used for RNA isolation.

RNA concentrations were determined by absorbance at 260 nm and verified by nondenaturing agarose gel electrophoresis and ethidium bromide staining as described in Thompson, C. B. et al., *Nature* 31 4:363–366 (1985). Equal quantities of total RNA were electrophoretically separated in 1% formaldehyde-agarose gels containing 0.5 μg/ml ethidium bromide and transferred to derivatized nylon membranes (Zeta-Probe, BioRad, Richmond, Calif.) as described in Elder, J. T. et al., *J. Invest. Dermatol.* 94:19–25 (1990) and Maniatis, T. et al., *Molecular Cloning: A Laboratory Manual, Cold Spring Harbor Laboratory*, Cold Spring Harbor, N.Y. (1982). Filters were baked 2 hours at 80° C. in vacuo, then prehybridized for 2–4 hours at 42° C. in 50% formamide, 5×SSC, 50 mM sodium phosphate, pH 7.0, 1×Denhardt's solution, 250 μg/ml yeast tRNA, 100 μg/ml sonicated herring sperm DNA and 1% SDS. Hybridization was carried out for 18–24 hours at 42° C. in the same buffer containing 10% dextran sulfate. Filters were washed twice for 10 minutes in 2×SSC, 0.1% SDS at room temperature, then twice for 20 minutes in 0.1×SSC, 0.1% SDS at 56° C. Autoradiography was performed using intensifying screens at −70° C. Filters were stripped by boiling 2×10 minutes in 0.1×SSC, 0.5% SDS. Hybridization probes were prepared by random priming (see Feinberg, A. P. et al., *Anal. Biochem.* 132:6–13 (1983)) of low melting agarose-purified insert fragments from the human CRABP-I PCR product, the CRABP-I cDNA (λf1.1) and rat cyclophilin. See Danielson, P. E. et al., *DNA* 7:261–267 (1988).

Autoradiograms were quantitated using a laser densitometer (LKB Model 2202) coupled to a Hewlett-Packard 3390 A integrator. Only exposures which were in the linear range of densitometric response were used. When appropriate, autoradiographic intensities were normalized to cyclophilin. See Elder, J. T. et al., *J. Invest. Dermatol.* 94:19–25 (1990). Statistical analysis of data was performed by one way analysis of variance using Scheffes correction for multiple comparison and a two-tailed hypothesis.

RESULTS

Cloning of human CRABP-I and CRABP-II

Using PCR and degenerate primers derived from bovine and mouse CRABP-I, a 436 base pair (bp) product was obtained, subcloned and sequenced. The predicted amino acid sequence of the PCR product was found to be 99.3% homologous to the mouse and bovine CRABP-I sequences. See Nilsson, M. H. L et al., *Eur. J. Biochem.* 173:45–51 (1988); and Stoner, C. M. et al., *Cancer Res.* 49:1497–1504 (1989). The PCR product was used to screen a human skin library and a human skin fibroblast library. Five clones were isolated from the skin fibroblast library (λf1.1, λf3.1, λf5.1, λf5.4 and λf5.6). Two clones (λf1.1, λf3.1) were sequenced and found to be identical. The predicted amino acid sequences of these clones were found to be 77.4% similar to human CRABP-I and 93.5 % similar to the recently cloned mouse CRABP-I. See Giguere, V. et al., PNAS (USA) 87:6233–6237 (1990). Because of the high homology to the mouse CRABP-II, clone λf1.1 was designated as human CRABP-II. A third clone λf5.1 was partially sequenced and found to be a shorter clone, with a sequence identical to human CRABP-II. No CRABP-I clones were isolated from the skin fibroblast library. Two clones were isolated from the skin library and found to contain shorter inserts, one with a sequence identical to human CRABP-II (λs2.1) and one with a sequence identical to human CRABP-II (λs3.1).

SEQ ID NOS: 1 and 2 in the Sequence Listing represent the cDNA nucleotide and predicted amino acid sequences of human CRABP-II, respectively. The translation initiation site was assigned to the first methionine codon corresponding to nucleotides 99–101. An open-reading frame of 138 amino acids was found, predicting a polypeptide of $M_r$ 15,693. The 3' untranslated region was found to contain a polyadenylation signal (ATTAAA) see nucleotides 911 to 916 of SEQ ID NO:1) and a poly(A) tract of 1 (λf1.1) to 25 (λf5.1). SEQ ID NOS: 3 and 4 represent the cDNA nucleotide and predicted amino acid sequence of CRABP-I, respectively.

Comparison of amino acid sequences of CRABP

The amino acid sequence comparison of CRABP-I and CRABP-II is presented in FIG. 2. Panel A is a comparison of the amino acid sequences for human (h) and mouse (m) CRABP. The predicted amino acid sequences of mouse and human CRABP-I and mouse CRABP-II were aligned with human CRABP-II. Dashes (—) represent identity to human CRABP-II. One gap as indicated by an asterisk (*) was introduced in the human and mouse CRABP-I sequences for maximum alignment. Panel B of FIG. 2 is the sequence comparison of the NH$_2$-terminal ends of human (h), mouse (m), rat (r), CRABP-I and CRABP-II. Residues dissimilar to human CRABP-II are boxed.

The amino acid sequence comparison presented in FIG. 2, (See SEQ ID NOS:2,4 and 11–16) Panel A, reveals a 73.7% overall degree of identity between mouse CRABP-I (Stoner, C. M. et al., *Cancer Res.* 49:1497–1504 (1989); Giguere, V. et al., PNAS (USA) 87:6233–6237 (1990)) and between human CRABP-I and human CRABP-II. Human CRABP-I and mouse CRABP-I displayed an overall identity of 99.3%, with a single amino acid substitution (amino acid residue 86, Ala instead of Pro), while human CRABP-II and mouse CRABP-II were 93.5% identical. Human and mouse CRABP-II displayed 9 amino acid differences with the following amino acids in the human sequence: residue 19⁻Leu,22⁻Val,27⁻Val,29⁻Leu,48⁻Gly,68⁻Val, 91⁻Glu, 99⁻Lys and 111⁻Thr. In 6 of the 9 amino acid differences seen between human CRABP-II and mouse CRABP-II (residues 19, 29, 48, 68, 91 and 111 ), the human sequence was identical to CRABP-I.

The NH$_2$-terminal amino acid sequences of two CRABPs from neonatal rat (Bailey, J. S. et al., *J. Biol. Chem.* 263:9326–9332 (1988)) and chicken embryos (Kitamoto, T. et al., *Biochem. Biophys. Res. Comm.* 157:1302–1308 (1988) have been reported and were also compared to human CRABP-I and CRABP-II. As shown in FIG. 2, Panel B, there were no amino acid differences between the NH$_2$-terminal regions of rat, chicken, mouse and human CRABP-I, whereas several differences appeared between the CRABP-IIs.

SPECIFIC EXAMPLE 2. Expression of Human CRABP

Expression of human CRABP in human skin in vivo

Volunteers were treated with 0.1% RA cream or control treatments under Occlusion for various time intervals. Keratome biopsies consisting mostly of epidermis (see Voorhees, J. J. et al., *Arch. Dermatol.* 105:695–701 (1972)) were obtained, and used to prepare total RNA which was subsequently analyzed by blot hybridization. The autoradiograms of the RNA blots derived from three individuals are shown in FIG. 3. Total RNA (40 μg per lane) was hybridized against the human CRABP-II or cyclophilin cDNA probes as described above. Each volunteer was treated topically for 16 hours prior to biopsy as follows: (a) no treatment, (b) RA vehicle or (c) 0.1% RA cream in RA vehicle under occlusion with plastic wrap. Mobilities of ribosomal RNAs are indicated to the left of the blots.

CRABP-II transcripts were detectable in untreated skin as well as skin treated with vehicle, as shown in FIG. 3. CRABP-II transcripts, were markedly (16.1-fold) and significantly ($p<0.004$, n=4) induced in RA treated relative to untreated skin. Similar, albeit less marked, inductions were observed after 4 days of IRA treatment (8.3±2.9-fold, n=6). Induction did not occur after 4 hours, but was evident after 12 hours of treatment. Consistent with our ability to amplify CRABP-I from human skin RNA, faint CRABP-I probe hybridization was observed in some but not all blots of human skin RNA samples after prolonged autoradiographic exposure (data not presented in Figures). However, CRABP-I transcripts were usually undetectable under exposure conditions sufficiently sensitive to detect single copy DNA sequences from 10 μg human genomic DNA. CRABP-I and CRABP-II cDNA probes detected distinct band patterns using genomic DNA digested with BamHI, EcoRI, HindIII and PstI, demonstrating the specificity of these probes under our hybridization conditions (data not presented in Figures).

Expression of CRABP in human fibroblasts

Treatment of human dermal fibroblasts with RA resulted in a marked (approximately 15-fold) and significant (P $<0.04$) induction of human CRABP-II mRNA after treatment of five independent dermal fibroblast strains with $3\times10^{-7}$ or $3\times10^{-6}$ M RA for 24 or 48 hours as shown in FIG. 4. Results shown are derived from nine independent experiments involving five dermal fibroblast lines prepared from three Individuals as described above and three diploid human lung fibroblast lines (LL47, CCD-18Lu, and CCD-16Lu). RNA blot hybridizations (20 μg total RNA/lane) were quantitated by laser densitometry and normalized to the control gene, cyclophilin, as described in Elder, J. T. et al., *J. Invest. Dermatol.* 94:19–25 (1990). At confluence, medium was changed and cells were treated with RA dissolved in dimethyl sulfoxide at the concentrations and for the times Indicated beneath the Figure. Data are expressed as fold induction±SEM, relative to the average of duplicate dishes treated with dimethyl sulfoxide alone for 4 hours *p<0.05, **p<0.005. The relevant autoradiographic bands from two representative experiments comparing dermal and lung fibroblasts are shown in the inset.

As shown in FIG. 4, CRABP-II mRNA was not significantly induced by RA in three strains of human lung fibroblasts, suggesting that this response may be tissue specific. Induction of human CRABP-II transcripts by RA was dose-dependent over the range of 3 $\times 10^{-10}$ to $3 \times 10^{-7}$ M RA (data not presented in Figures). In contrast, CRABP-I transcripts were undetectable in dermal and lung fibroblasts and were not induced by RA, whereas genomic DNA blots hybridized in parallel were positive.

Expression of CRABP in human keratinocytes

Figure 5A:
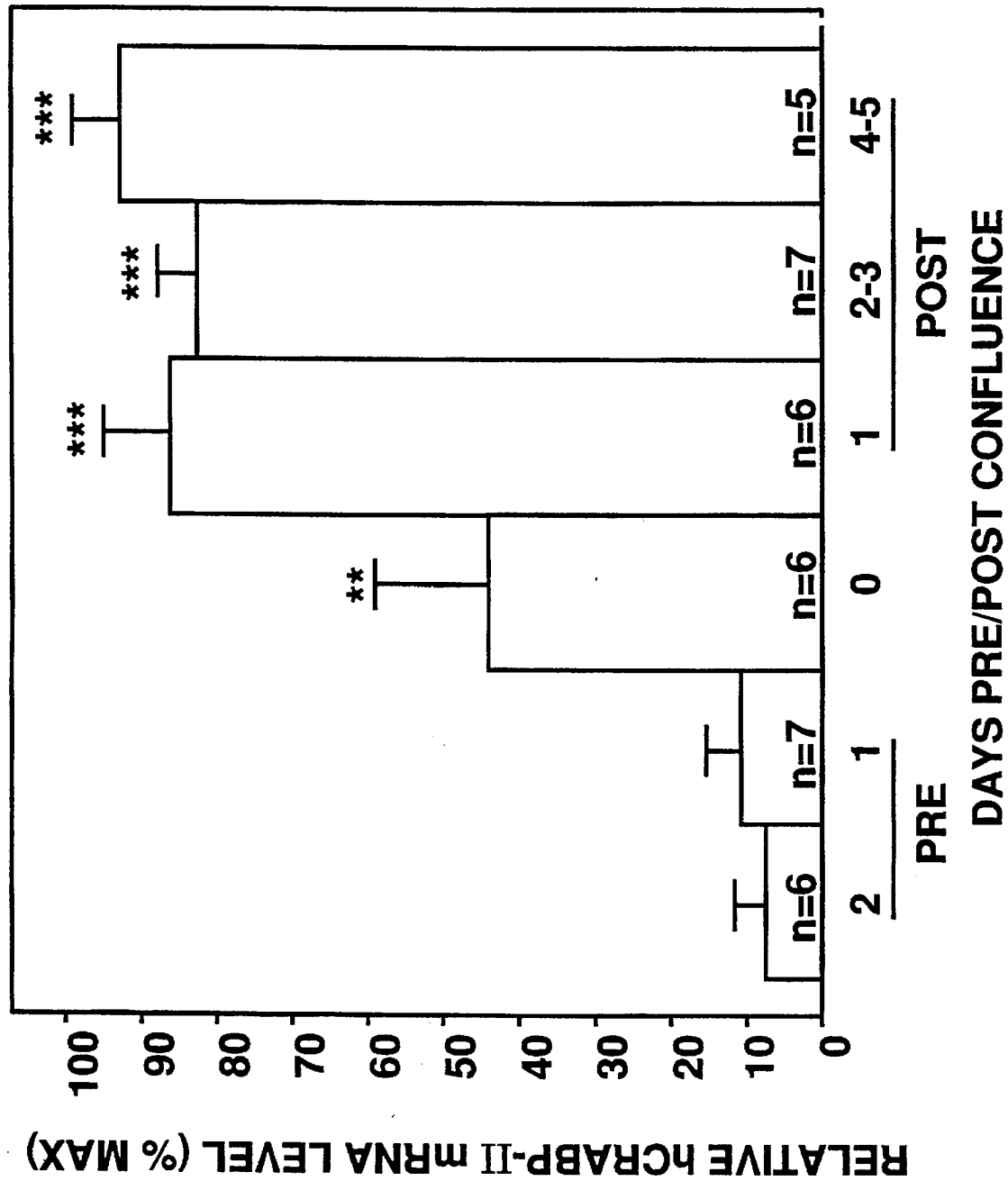
Figure 5C:
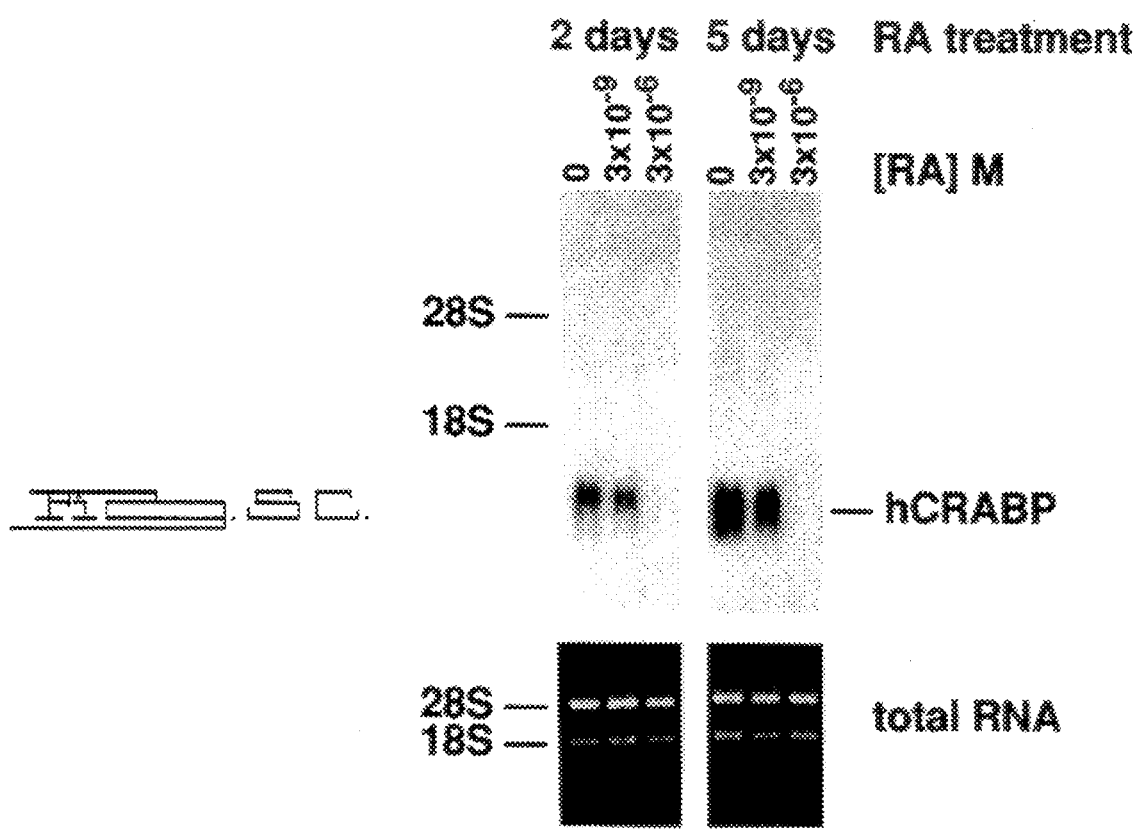

As shown in FIG. 5, CRABP-II mRNA was markedly and significantly Induced in cultured adult human keratinocytes when cells reached confluence, and remained elevated in the postconfluent state. FIG. 5A summarizes the results obtained for seven independent keratinocyte strains. Third passage normal adult human keratinocytes were grown in KGM containing 0.15 mM $CaCl_2$, and medium was changed every other day. At the indicated number of days pre- or postconfluence, total RNA was prepared and analyzed for human CRABP-II mRNA by blot hybridization and densitometry. Data are expressed as percent maximal expression for any given strain of keratinocytes, as the absolute level of human CRABP-II mRNA was variable from strain to strain. Error bars represent±SEM. $p<.005$, *$p<0.0005$ relative to cells at 2 days preconfluence.

CRABP-II mRNA was also markedly induced in subconfluent cultures by raising the calcium concentration in the medium from 0.15 mM to 2 mM, as illustrated for a representative strain of keratinocytes in FIG. 5B. At 20–30% confluence, the medium was changed to KGM or KGM containing 2 mM $CaCl_2$ in the presence or absence of $3 \times 10^{-9}$ M RA and maintained for the indicated number of days, with medium change every other day. Mobilities of 28S and 18S ribosomal RNAs are indicated to the left. FIG. 5C shows the effects of prolonged treatment with high concentrations of RA on CRABP-II mRNA levels. The same experiment described for FIG. 5B was conducted above, except that cells were treated with or without $3 \times 10^{-6}$ M RA for 2 to 5 days, as indicated above the autoradiograms. Mobilities of 28 and 18S ribosomal RNAs are indicated to the left. FIGS. 5A and B show the results representative of four independent experiments.

As shown in FIG. 5B, treatment of keratinocytes for prolonged periods of time with low concentrations of RA ($3 \times 10^{-9}$ M) had no detectable effect on CRABP-II mRNA levels. However, as shown in FIG. 5C, prolonged treatment of subconfluent keratinocytes with high concentrations of RA ($3 \times 10^{-6}$ M) reduced CRABP-II mRNA to undetectable levels. Hybridization of the same blot against CRABP-I prior to its hybridization against CRABP-II failed to detect CRABP-I transcripts, whereas genomic DNA blots hybridized in parallel were positive (data not presented in Figures).

SPECIFIC EXAMPLE 3. Alternate Cloning Scheme

The CRABP-II cDNA probe was cloned by PCR from retinoic acid (RA) treated human skin using the CRABP-II forward (SEQ ID NO:9) and reverse (SEQ ID NO:10) degenerate primers shown in FIG. 1B, derived from mouse CRABP-II mRNA sequence. See Giguere, V. et al., PNAS (USA) 87:6233–6237 (1990). BamHI restriction sites were Included in the forward and reverse primers to aid in subsequent cloning.

RA-treated human skin was used as the source of RNA for reverse transcription and PCR amplification. Total RNA was extracted from epidermal keratomas as described in Elder, J. T. et al., *J. Invest. Dermatol.* 94:19–25 (1990), and reverse transcribed as described In Maniatis, T. et al., *Molecular Cloning: A Laboratory Manual,* Cold Spring Harbor Laboratory, Cold Spring Harbor, N.Y. (1982). During each PCR cycle, samples were heated to 94° C. in 1 minute and maintained for 30 seconds, cooled to 50° C. for primer annealing, and then heated in 1 minute duration to 72° C. and kept at that temperature for a further 30 seconds to allow template extension. The PCR product was further purified (Geneclean, BIO 101 Inc.), digested with BamHI and cloned into BamHI digested PGEM 3Z plasmid (Promega Inc., Madison, Wis.). The PCR fragment was Initially identified as CRABP-II by digestion with PstI restriction enzyme that cleaved the DNA at the same position as that described in the mouse CRABP-II mRNA. The clone was sequenced and found to represent the major portion of the mature human analogue of the mouse CRABP-II. The cDNA probe was hybridized to human RNA prepared from skin of human volunteers topically treated with RA for 4 and 12 hours. Induction of CRABP-II mRNA was observed in skin which had been RA-treated for 12 hours, but not skin treated for only 4 hours (data not illustrated in Figures).

SPECIFIC EXAMPLE 4. CRABP Mammalian Expression Vectors and Constructs

CRABP-I was excised from the Bluescript phagemid (Stratagene) cloning vector and inserted between the XbaI and BamHI sites of the eukaryotic expression vector pSVL (Pharmacia) in forward orientation (pSVLCRABP-I). CRABP-II was excised from the Bluescript phagemid (Stratagene) cloning vector and inserted into the EcoRI site of the eukaryotic expression vector pSG5 (Stratagene) in forward (pSG5CRABP-II) or reverse orientation (pSG5CRABP-IIAS). The orientation of the insert was determined by restriction analysis.

CV-1 cells are grown in Dulbecco's modified Eagles medium (DMEM) containing 10% fetal calf serum. CV-1 are monkey kidney calls derived from the CV-1 call line which do not express T cell antigen. The day before transfection, calls are seeded on tissue culture dishes in DMEM containing 10% charcoal treated fetal calf serum (ChFCS). Cells are contransfected using the calcium phosphate co-precipitation technique essentially as described in Rosenthal, N., *Meth. Enzymol.* 152:704–720 (1987) with CRABP-I (pSVLCRABP-I) or CRABP-II (pSG5CRABP-II) expression vector. 24 hours after transfection, calls are trypsinized and suspended in medium, pelleted and washed once with 40 mM Tris-C1, pH 7.6 containing 150 mM NaCl and 1 mM EDTA. A cytosolic fraction is prepared on cell lysates by centrifugation at 100,000×g for 1 hour.

SPECIFIC EXAMPLE 5. Bacterial Production of Human CRABP

For CRABP-I, the nucleotide sequence of CRABP-I is changed at position 9 (T to G) and 13 (C to T) to create a StuI site, using synthetic oligonucleotides and the polymerase chain reaction. For CRABP-II, the nucleotide sequence of CRABP-II Is changed at position 100 (T to G) and 104 (C to T) to create a StuI site, using synthetic oligonucleotides and the polymerase chain reaction. The mutated CRABP cDNAs are then cut with StuI and ligated into the StuI and EcoRI sites of the bacterial expression vector pMAL-c (New England Biolabs). Bacteria is transformed and the maltose-binding protein (MBP)-CRABP fusion proteins are expressed in large quantities. The MBP-CRABP fusion protein is purified by affinity chromatography on any amylose column (New England Biolabs). CRABP lacking the first methionine is released from MBP by digestion with factor Xa (New England Biolabs) and purified from MBP by a second passage over an amylose column.

Spectrofluorimetric methods are used to study the affinities and binding stoichiometries of purified human CRABP-I and CRABP-II for a variety of ligands. The capacity of ligands to bind to CRABP-I or CRABP-II is assessed by monitoring their ability to quench the native fluorescence of this protein.

SPECIFIC EXAMPLE 6. Production of Antibodies

Peptides corresponding to amino acids 94 to 104 in the CRABP-I and CRABP-II proteins have been synthesized using the multiple antigenic peptide method as generally described in Posnett, D. N. et al., *Meth. Enzymol.* 178:739–746 (1989), eliminating the need for conjugation to a carrier protein. This region of the two CRABPs has a low homology and is most probably situated on the outside of the proteins based on hydrophobicity and surface probability calculations.

The peptides were injected into chickens for production of egg IgY. The resulting antibodies, if not specific, are adsorbed to peptides (CRABP-I antibodies to CRABP-II peptides and the reverse) immobilized on a sepharose gel to enhance specificity. Once monospecific antibodies are obtained, the expression and regulation of CRABP-I and CRABP-II proteins in human skin and skin cells is examined quantitatively by Western blot analysis and semi-quantitatively by immunocytochemistry. The pattern of expression and regulation of CRABP-II (and CRABP-I) by RA in normal and psoriatic skin will provide insight into the function of CRABPs.

Antibodies to CRABP-I and CRABP-II, or binding fragments (e.g. F'(ab)) thereof, and the purified proteins obtained as described above can be used to monitor levels of CRABP-I and CRABP-II in normal and pathological states by using immunological techniques known to those skilled in the art. For example, patient skin tissue can be assayed with antibody specific for human CRABP-I or CRABP-II to determine the presence and levels of CRABP by ELISA, Western blot analysis or immunochemistry essentially as described in Busch, C. et al., *Meth. Enzymol.* 189:315–324 (1990).

SPECIFIC EXAMPLE 7. Reporter Assay System

CV-1 cells are grown in Dulbecco's modified eagles medium (DMEM) containing 10% fetal calf serum. The day before transfection, cells are seeded on tissue cultured dishes in DMEM containing 10% charcoal treated fetal calf serum (CHFCS). Cells are cotransfected using the calcium phosphate co-precipitation technique with 0.6 mg of human retinoic acid receptor (hRAR) expression vectors (hRARα0, hRARβ0 or hRARλ0), a reporter plasmid and a p-galactosidase expression vector (pcH110, Pharmacia) used as an internal control to normalize for variations in transfection efficiency essentially as described in Astrom, A. et al., *Biochem. Biophys. Res. Comm.* 173:339–345 (1990). Cells are also cotransfected with CRABP-I (pSVLCRABP-I) or CRABP-II (pSG5CRABP-II) expression vectors of pSVL (Pharmacia) as a control. The reporter plasmid (TRE)$_3$-tk-CAT is constructed by ligating synthetic oligonucleotides encoding three palindromic thyroid hormone responsive elements (TRE) ((TCAGGTCATGACCTGA)$_3$) (SEQ ID NO:17) flanked by HindIII and BamHI sites on the 5' and 3' ends respectively and cloned into the HindIII - BamHI cloning sites of the plasmid pBLCAT2. 24 hours after transfection, cells are washed once with DMEM, and medium (DMEM, 10%ChFCS) containing different concentrations of ligands are added to the cells. 24 hours later the cells are trypsinized and suspended in medium, pelleted and washed once with 40 mM Tris-Cl, pH 7.6 containing 150mM NaCl and 1 mM EDTA. Cell lysates are prepared by three consecutive freeze-thaw cycles and β-galactosidase and CAT-activities are determined by a xylene extraction method. The effect of coexpression of CRABP-I or CRABP-II on RAR transcriptional activation for different ligands can now be determined as described below.

An alternative reporter assay in which a recombinant adenovirus system is used to coinfect cells in culture may also be employed to measure transcriptional activation by retinoids essentially as described in Shih, E. et al., *Mol. Endocrinol.* 5:300–309 (1991). In such a system, two mutually dependent viruses, one containing a receptor transcription unit and the second containing a gene responsive element are coinfected into receptor-deficient cells such as CV-1. For example, two mutually dependent adenoviruses, one containing a human glucocorticoid receptor transcription unit and the other a glucocorticoid responsive element linked to the firefly luciferase gene, or one containing rat thyroid hormone receptor α and the other the luciferase gene, can be utilized in the practice of the assay. Hormone-induced transcription is then quantitated after infection from cells coinfected with the complementary virus pair.

SPECIFIC EXAMPLE 8. Ligand Binding Assays

Since the amino-acid homology between CRABP-I and CRABP-II is only 77%, it is important to determine the ligand binding properties of these two proteins. There are several reports on the lack of correlation between biological activity and affinity of retinoids to CRABP. Darmon, M. et al., *Skin Pharmacol.* 1:161–175 (1988). Most of these studies have used extracts from rat testis containing mostly rat CRABP-I as the source of CRABP. In contrast, we are expressing the CRABP-I and CRABP-II cDNAs in mammalian cells.

Availability of cloned human CRABP-I and II thus improves previous systems for identification of tissue-specific ligands. This also makes identification of ligands interacting with CRABP possible, in addition to nuclear receptors. Ligands for testing include, but are not limited to didehydro-RA, RA and its metabolites, 4-hydroxy-RA, 4-oxo-RA, and 5,6-epoxy-RA as well as compounds previous reported not to bind to CRABP, e.g. CD-394. Darmon, M. et al., *Skin Pharmacol.* 1:161–175 (1988). Availability of CRABP amino-acid sequences or proteins provide the means to select more tissue-specific drugs for repair of photoaging skin, psoriasis, acne, skin cancer, leukemia, diseases of keratinization, osteoperosis, rheumatoid sclerosis, and other conditions.

Soluble protein from CV-1 cells transfected with CRABP-I (pSVLCRABP-I) or CRABP-II (pSG5CRABP-II) expression vectors obtained as described above is incubated with [$^3$H] retinoic acid at 4° C. overnight. Free ligand is separated from bound ligand by size fractionation on a GF 250 column (DuPont Pharmaceuticals) connected to a FPLC system (Pharmacia). The amount of specific binding is determined by incubating samples with an excess of cold retinoic acid. The affinity of CRABP-II for retinoic acid can be determined by titrating with increasing amounts of [$^3$H] Retinoic acid.

The relative affinity for other ligands is determined in competition assays in the same system. A fixed amount of CRABP-I or [$^3$H] retinoic acid is incubated with soluble protein from CV-1 cells expressing CRABP-II together with increasing amounts of other possible ligands.

SPECIFIC EXAMPLE 9. Hybridization Assay

Availability of cloned human CRABP-I and CRABP-II cDNAs makes it possible to determine the relative expression of these two genes in normal and pathological states. For example, RNA is isolated from tissue biopsies and cultured cells by guanidinium isothiocyanate lysis and ultracentrifugation as previously described in Elder, et al., *J. Invest. Dermatol.* 94:19–25 (1990). Equal quantities of total RNA can be separated on 1% formaldehyde-agarose gels and transferred to nylon membranes. After baking for 2 hours at 80° C., filters can be hybridized to agarose-purified CRABP-I or CRABP-II cDNAs labeled by random priming. The amount of CRABP mRNA in a tissue can be determined after quantitation of autoradiograms by laser-densitometry as described (Elder, et al., *J. Invest. Dermatol.* 94:19–25). it will be appreciated that CRABP-I and II oligonucleotides (typically 8–15 residues long) may also be utilized as probes in hybridization assays if of a sufficient length to bind complementary sequences.

SPECIFIC EXAMPLE 10. Examination of Function of Human CRABP

Receptor assay

The most important and difficult issue to resolve regarding the CRABPs is their function. It has been suggested that CRABP transports RA to the nucleus (Takase, S. et al., *Arch. Biochem. Biophys.* 247:328–334 (1986)) or that CRABP remains in the cytoplasm, thereby preventing RA from moving to the nucleus. Maden, M. et al., *Nature* 335:733–735 (1988). One way of addressing this issue is to express increasing amounts of CRABP-I and CRABP-II in CV-1 cells together with the RARs and a reporter gene containing a retinoic acid responsive element, as described above. If CRABP transports RA to the nucleus an enhancement of reporter gene activity at low concentrations of RA may be seen. On the other hand, if CRABP sequesters RA a decrease in response will be seen.

Overexpression

CRABP-I and CRABP-II is overexpressed in fibroblasts and keratinocytes. Cells will be transfected with CRABP expression vectors (pSVLCRABP-I or pSG5CRABP-II) as described above, using Lipofectin (BRL) essentially as described by the manufacturer. In fibroblasts the effect of CRABP overexpression on Induction of the RAR-β gene by RA is studied. It has been shown that RAR-β mRNA is induced by RA in skin fibroblasts, and it is known that this gene is directly regulated by the RARs. See DeThe, H. et al., *Nature* 343:177–180 (1990). The RAR-β gene acts as an "endogenous reporter gene" for RAR induction. In proliferating keratinocytes the effect of overexpression of CRABPs on markers of differentiation is studied.

Translation blocking

Translation of CRABP-II is blocked in fibroblasts and keratinocytes by transfecting the cells with an expression vector construct having the CRABP-II cDNA in a reverse orientation. This produces an anti-sense mRNA that is able to hybridize to the endogenous CRABP-II mRNA, thereby blocking translation. The effect of antisense expression in fibroblasts and keratinocytes is studied the same way as described for overexpression.

Effect of CRABP on RA metabolism

The involvement of the cellular retinol binding protein (CRBP) in delivering retinol to the appropriate metabolic enzyme in rat liver microsomes has been described. Ong, D. E. et al., *J. Biol. Chem.* 263:5789–5796 (1988). Since the CRABPs belong to the same family of binding protein as CRBP, it is possible that they also are involved in the metabolism of their ligands. RA is metabolized by the cytochrome P-450 monooxygenase system present in the endoplasmic reticulum. Bossche, H. et al., *Skin Pharmacol.* 1:176–185 (1988). CRABP may function by Increasing the interaction of RA with cytochrome P-450. Another possibility is that RA is not the natural ligand for CRABP-II, but rather one of the metabolites. If CRABP-II for example, binds 4-hydroxy-RA (as determined by ligand-binding studies) with a higher affinity than RA, it is possible that CRABP-II increases cytochrome P-450 mediated metabolism by decreasing product concentration. Whether the CRABPS are involved in RA metabolism or not is tested by incubating skin microsomes with increasing amounts of RA and of expressed and purified CRABP-I or CRABP-II. The effects of CRABPs on RA metabolism is assayed by HPLC.

SPECIFIC EXAMPLE 11. Cloning and Sequencing of Human CRABP-II Gene and Transcription Studies

MATERIALS AND METHODS

Cloning of the human CRABP-II gene

To isolate the CRABP-II gene, approximately $5 \times 10^5$ recombinants from a human placenta genomic DNA library in Lambda FIX II (Stratagene Inc., LaJolla, Calif.) were screened using the human CRABP-II cDNA as a probe. Aström, A. et al., *J. Biol. Chem.* 266:17662–17666 (1991). One positive clone was isolated, purified and restriction mapped. Parts of the insert were subcloned into Bluescript phagemid SK (Stratagene Inc., LaJolla, Calif.). The sequence of the gene was determined on both strands after subcloning into M13 vectors by dideoxy chain termination using modified T7 polymerase (Sequenase, U.S. Biochemical Corp.) and synthetic oligonucleotides. Sanger, F. et al., *PNAS (USA)* 74:5463–5467 (1977). Exon positions were determined by restriction mapping and sequencing.

Cell culture

Human dermal fibroblast cultures were prepared from punch biopsies of buttock skin and propagated in Dulbecco's modified Eagle's medium containing 10% calf serum. Harper, R. A. et al., *Science* 204:526–527 (1979).

Northern analysis of mRNA

RNA was isolated from cultured human skin fibroblasts by guanidinium isothiocyanate lysis and ultracentrifugation as previously described. Elder, J. T. et al., *J. Invest. Dermatol.* 94:19–25 (1990). RNA concentrations were determined by absorbance at 260 nm and equal quantities of total RNA were electrophoretically separated in 1% formaldehyde-agarose gels containing 0.5 μg/ml ethidium bromide. The RNA was transferred to nylon membranes (Zeta-Probe, BioRad, Richmond, Calif.) as described. Elder, J. T. et al., *J. Invest. Dermatol* 94:19–25 (1990); Maniatis, T. et al., *Molecular Cloning: A Laboratory Manual* (Cold Spring Harbor Laboratory, Cold Spring Harbor, N.Y.) (1982). Filters were basked 2 hours at 80° C. in vacuo, then prehybridized for 2–4 hours at 42° C. in 50% formamide, 5×SSC (1×SSC=150 mM NaCl, 15 Mm sodium citrate), 50 mM sodium phosphate, pH 7.0, 1×Denhardt's solution, 250 μg/ml yeast tRNA, 100 μg/ml sonicated herring sperm DNA and 1% SDS. Hybridization was carried out for 18–24 hours at 42° C. in the same buffer. Filters were washed once in 0.2×SSC, 0.1% SDS at room temperature, then twice for 20 min in 0.2×SSC, 0.1% SDS at 56° C., and finally once for 20 min in 0.1×SSC, 0.1% SDS at 56° C. Autoradiography was performed using intensifying screens at −70° C. Filters were stripped by boiling 2×10 min in 0.1×SSC, 0.1% SDS. Hybridization probes were prepared by random priming (Boeringer Mannheim) of purified insert fragments from human CRABP-II cDNA (λf1.1) rat cyclophilin and RAR-γ, Aström, A. et al., *J. Biol. Chem.* 266:17662–17666 (1991); Danielson, P. E. et al., DNA 7:261–267; Elder, J. T. et al., *J. Invest. Dermatol* 96:425–433 (1991). Quantitation of mRNA levels were performed using a phosphorimager (Molecular Dynamics).

Primer extension analysis

RNA was isolated from untreated and RA treated skin fibroblasts as described. Aström, A. et al., *J. Biol. Chem.* 266:17662–17666 (1991). A synthetic oligonucleotide 5' CTAGGCTGGAGCACTGGACACTGTC 3' (SEQ ID NO:18) complementary to position 80–104 in the gene was used as an extension primer. 10 μg of total RNA was heated for 10 minutes at 70° C. together with $^{32}$p 5' end-labeled primer. The mixture was allowed to cool to 30° C. over 30 minutes and then kept at 30° C. for an additional 30 minutes.

To the mixtures were added (final concentration) 50mM Tris-HCl (pH 8.3), 75 mM KCl and 3 mM $MgCl_2$, 5 mM DDT and 250 mM of dATP, dCTP, dGTP, d'Fi'P in 40 μl total volume. The reactions were started by the addition of 200 u Superscript RNase H⁻ (GIBCO, Bethesda Research Laboratories) and incubated for 90 minutes at 42° C. Samples were phenol/chloroform-extracted, ethanol-precipitated, resuspended in formamide dye and after heating to 75° C. for 5 minutes, separated on a 6% sequencing gel.

Transcriptional analysis

Cultured human skin fibroblasts were grown to confluency on 150 mm tissue culture dishes as described. Astrom, A. et al., *J. Biol. Chem.* 266:17662–17666 (1991). Cells were then treated for various time-points with 1 μM RA in pre-warmed and equilibrated Dulbecco's modified Eagle's medium containing 10% fetal calf serum. Nuclei for each time-point were isolated from four dishes after incubation in h/sis buffer containing 0.5% NP-40 as described. Greenberg, M. E. et al., *Nature* 311:433–438 (1984). Nuclear run-on experiments were performed with [α-$^{32}$P] UTP (DuPont-New England Nuclear, 800 Ci/mmol) as described. Antras, J. et al., *J. Biol. Chem.* 266:1157–1161 (1991). Equal amounts of radioactivity (0.5–1×10$^7$ cpm) were hybridized to nitrocellulose filters containing 5 μg of each plasmid. After hybridization for 72 hours at 42° C., the filters were washed twice with 2×SSC at 37° C. for 15 minutes and treated for 30 minutes at 37° C. in 2×SSC containing 5 μg/ml RNase A. The filters were then washed twice for 15 minutes in 2×SSC, 0.5% SDS at 42° C. and once for 30 minutes in 0.5×SSC, 0.5% SDS at 42° C. A final wash was carried out in 0.1×SSC, 0.1% SDS for 30 minutes at 55° C. The amount of radioactivity present in each slot was determined using a phosphorimager (Molecular Dynamics) after over-night exposure and autoradiograms were exposed for 4–5 days at –70° C. with intensifying screens.

RESULTS

Cloning and characterization of the human CRABP-II gene

Figure 7:
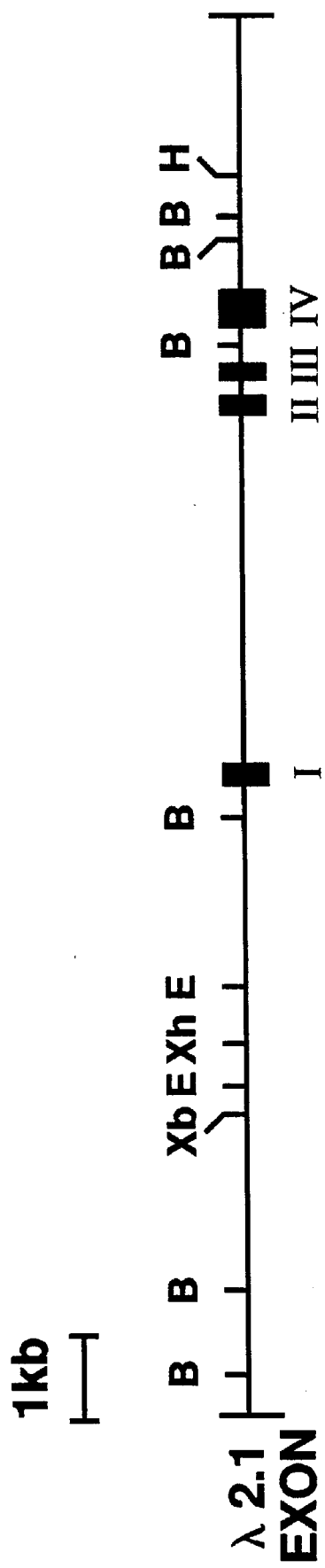
FIG. 7 is a restriction map of a bacteriophage lambda clone (λ2.1) isolated from a human placenta genomic library of the human CRABP-II gene with the exons indicated as filled boxes numbered I to IV.

Using the human CRABP-II cDNA as a probe, one bacteriophage lambda clone was isolated (λ2.1) from a human placenta genomic library. Restriction mapping and sequencing revealed that this clone contained the entire CRABP-II gene. A restriction map of λ2.1 is shown in FIG. 7. The gene is composed of four exons, interrupted by one large and two small introns. The overall size of the gene is approximately 6 kb.

DNA Sequence of the human CRABP-II gene

To characterize the CRABP-II gene, fragments spanning the entire gene, except for the first intron were subcloned into M13 vectors for sequence analysis. The nucleotide sequence and the deduced amino-acid sequence is presented in FIG. 8. The first three exons are small and range in size from 117 to 207 bp, with the fourth exon being the largest at 466 bp as demonstrated in FIG. 8. The exon sequences were found to be identical to the published cDNA sequence. Aström, A. et al., *J. Biol. Chem.* 266:17662–17666 (1991 ). All splice junctions contained the expected GT splice donor and AT splice acceptor.

Analysis of the 5' end of be human CRABP-II gene

Figure 9:
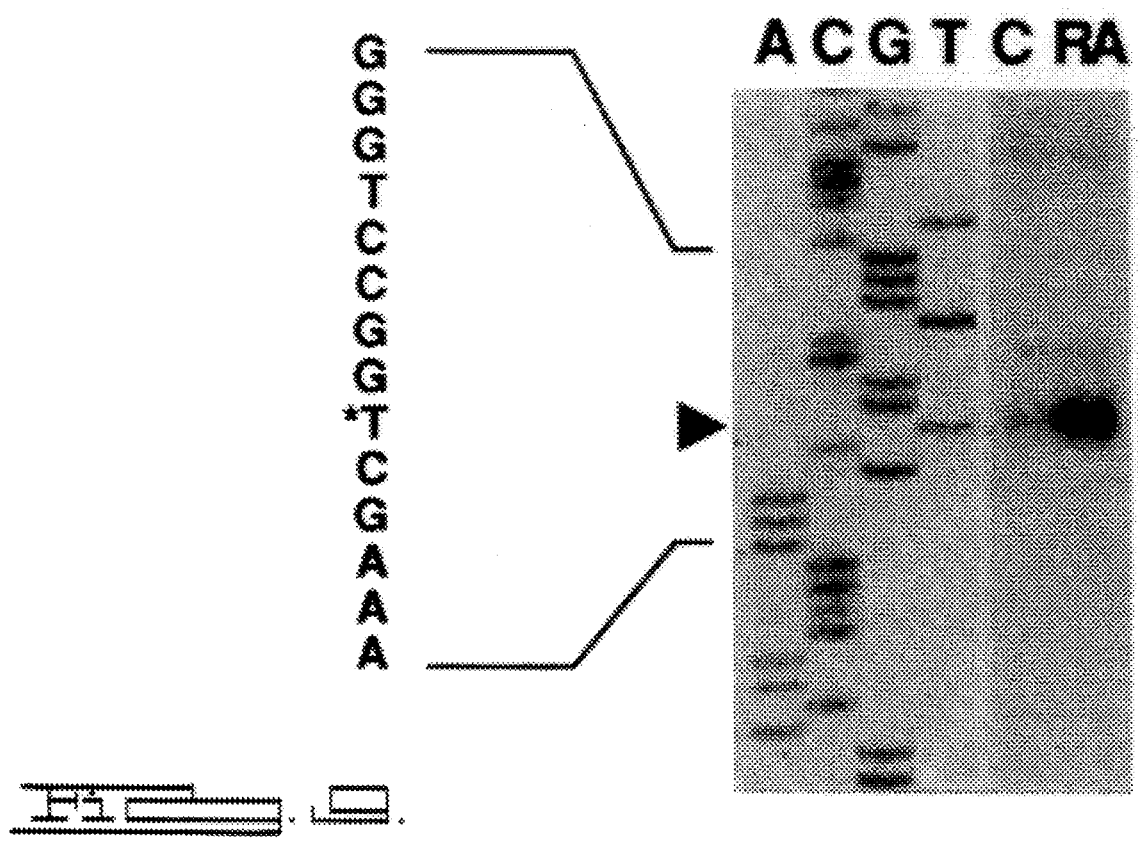
FIG. 9 illustrates the transcription start sites in the human CRABP-II gene as determined by primer extension analysis, with the major transcription site indicated by an arrow and the corresponding base in the sequence indicated by an asterisk (SEQ ID NO:17).

The 5' boundary of the first exon was determined by primer extension analysis. Using an oligonucleotide primer complimentary to position 80–104, a predominant reaction product was identified when mRNA from untreated cultured human skin fibroblasts were used, see FIG. 9. Comparison of the extension product with sequencing reactions originating from the same primer indicated that the major transcription initiation site should be assigned to the A residue 137 bp upsteam of the ATG. When fibroblasts were treated with 1 μM RA for 24 hours an increase in initiation at the A residue could be seen. In addition a second initiation product with the same intensity could be seen at –1.

Sequence analysis of the upstream region revealed a TATA box (TATAAA) at –31 and several potential regulatory elements including two potential AP2 binding sites at –631 and –402, and one potential SP1 site at –89 as demonstrated in FIG. 8. Mitchell, P. J. et al., *Cell* 50:847–861 (1987);, Kadonaga, J. T. et al., *Trends Bichem. Sci.* 11:20–23 (1986). In addition two sequences can be found that exactly match a binding site for the early growth response gene Krox-24 (Egr-1, zif268 or NGFI-A) at –579 and –116. Lemaire, P. et al., *Mol. Cell. Biol.* 10:3456–3467 (1990). In addition a direct repeat spaced by one bp (AGTTCAGGGTTCA) can be found in the upstream region of the gene at –454, with homology to the retinoic acid responsive element found in the RAR-$\beta_2$ gene. Umesono, K. et al., *Cell* 65:1255–1266.

Effects of RA on CRABP-II transcription rates and mRNA levels

To determine whether RA induction of CRABP-II mRNA seen in cultured human skin fibroblasts was due to increased transcription, nuclear run-on assays were performed using nuclei isolated from cultured human skin fibroblasts treated with RA for various periods of time. As seen in FIG. 10, RA caused a rapid transient increase in CRABP-II transcription, peaking at 2 hours and being almost back to control levels at 6 hours. However, there was no change In RAR-$\gamma$ and cyclophilin transcription, two genes known to be unaffected by RA in skin fibroblasts as demonstrated by FIG. 10. Edler, J. T. et al., *J. Invest. Dermatol.* 96:425–433 (1991). Quantitation and normalization to cyclophilin shows that CRABP-II transcription is induced approximately 6-fold after 2 hours of RA treatment. See FIG. 11.

This increase in transcription can account for the 6-fold induction of CRABP-II mRNA after 24 hours of treatment, as seen in FIG. 11. Induction of CRABP-II mRNA can be detected as early as 2 hours after addition of RA to cells, leveling out between 6 to 24 hours of treatment. However, a smaller increase can be seen between 24 and 48 hours. To determine whether RA is required to be present in the medium for maintaining the induced CRABP-II message levels after the transcription has occurred, human skin fibroblasts were treated with RA for 12 hours, after which the cells were washed two times and replaced with medium without any addition of RA. As can be seen in FIG. 11, removal of RA from the medium causes a decline of the CRABP-II message compared to cells treated with RA for the entire experiment.

Effects of cycloheximide or actinomycin D on the Induction of CRABP-II message

Experiments were performed to determine whether the addition of inhibitors of transcription or translation could inhibit the increase of CRABP-II mRNA produced by RA. Cycloheximide (10 μg/ml) or actinomycin D (2 μg/ml) were added simultaneously with RA (1 μM) and CRABP-II levels were determined after 2 hours. As can be seen in FIG. 12, cycloheximide down-regulated basal CRABP-II expression and blocked the RA induction. Cycloheximide had no effect on RAR-$\gamma$ expression or RA induction of RAR-β (FIG. 12), as previously reported. Nervi, C. et al., *Cell Growth Diff.* 1:535–542 (1990); DeThe, H. et al., *EMBO J.* 8:429–433. Actinomycin D, had no effect on basal levels of CRABP-II message, but completely blocked induction by RA. As controls, RAR-$\gamma$ was found to be down-regulated by actinomycin D, and RA induction of RAR-$\beta$ was completely blocked in agreement with previous reports. Nervi, C. et al., *Cell Growth Diff.* 1:535–542 (1990); DeThe, H. et al., *EMBO J.* 8:429–433 (1989).

Effects of cycloheximide on CRABP-II transcription rates

Since cyloheximide blocked RA induction of CRABP-II mRNA, run-on experiments were performed to see if protein synthesis was required for the induction of transcription. As can be seen in FIG. 13, addition of Cycloheximide at time 0 completely blocked IRA induction of CRABP-II gene transcription.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All publications and applications cited herein are incorporated by reference.

What is claimed is:

1. An isolated receptor deficient cell comprising an expression vector encoding human cellular retinoic acid binding protein-II, CRABP-II, an expression vector encoding an additional retinoid-binding protein, and a reporter gene functionally linked to a retinoid responsive element.

2. The isolated cell of claim 1, wherein the retinoid-binding protein is a nuclear retinoic acid receptor.

3. The isolated cell of claim 1, wherein the retinoid-binding protein is a retinoid X receptor.

4. A method for assaying binding of a ligand to human CRABP-II comprising the steps of:

a) transfecting a receptor deficient cell with a vector and a retinoid responsive element, wherein the vector comprises a plasmid or virus comprising a nucleic acid sequence encoding said human CRABP-II;

b) exposing the transfected cell to the ligand under conditions favorable for the binding of the ligand to human CRABP-II; and c) detecting the binding of the ligand to human CRABP-II.

5. The method of claim 4 wherein the retinoid responsive element further comprises a reporter gene functionally linked thereto and the binding is detected by assaying for the presence of the reporter gene product.

6. The isolated cell of claim 1, wherein the receptor deficient cell is a CV-1 cell.

7. The isolated cell of claim 4, wherein the receptor deficient cell is a CV-1 cell.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 924 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapien
        ( F ) TISSUE TYPE: skin
        ( G ) CELL TYPE: fibroblast ( v i i ) IMMEDIATE SOURCE:
        ( A ) LIBRARY: HUMAN SKIN FIBROBLAST LAMBDA GT11
        ( B ) CLONE: LAMBDA F1.1

( i x ) FEATURE:
        ( A ) NAME/KEY: CDS
        ( B ) LOCATION: 99..515
        ( D ) OTHER INFORMATION: /codon_start=99
            / citation=([1])

( i x ) FEATURE:
        ( A ) NAME/KEY: polyA_site
        ( B ) LOCATION: 924
        ( D ) OTHER INFORMATION: /citation=([1])

( i x ) FEATURE:
        ( A ) NAME/KEY: 5'UTR
        ( B ) LOCATION: 1..98
        ( D ) OTHER INFORMATION: /citation=([1])

( i x ) FEATURE:
        ( A ) NAME/KEY: 3'UTR
        ( B ) LOCATION: 516..924
        ( D ) OTHER INFORMATION: /citation=([1])

( i x ) FEATURE:
        ( A ) NAME/KEY: polyA_signal
        ( B ) LOCATION: 911..916
        ( D ) OTHER INFORMATION: /citation=([1])

( i x ) FEATURE:
        ( A ) NAME/KEY: terminator
        ( B ) LOCATION: 513..515
        ( D ) OTHER INFORMATION: /citation=([1])

( x ) PUBLICATION INFORMATION:
        ( A ) AUTHORS: Astrom, Anders
            Tavakkol, Amir
            Pettersson, Ulrika
            Cromie, Matthew Elder, James T.
Voorhees, John J.
(B) TITLE: Molecular Cloning of Two Human Cellular
Retinoic Acid-Proteins (CRABP)
(C) JOURNAL: J. Biol. Chem.
(G) DATE: 1991
(K) RELEVANT RESIDUES IN SEQ ID NO:1: FROM 1 TO 924

(x) PUBLICATION INFORMATION:
(A) AUTHORS: Astrom, Anders
Tavakkol, Amir
Elder, James T.
Pettersson, Ulrika
Cromie, Matthew
Voorhees, John J.
(B) TITLE: Cloning of CRABPII cDNA from Human Skin:
Retinoic Acid Induces Expression of CRABPII but
Not CRABPI in Human Skin in Vivo and in Dermal but
Not Lung Fibroblasts in Vitro
(C) JOURNAL: J. Invest. Dermatol.
(D) VOLUME: 96
(F) PAGES: 547-547
(G) DATE: April-1991

(xi) SEQUENCE DESCRIPTION: SEQ ID NO:1:

```
CCTGACGACC CGGCGACGGC GACGTCTCTT TTGACTAAAA GACAGTGTCC AGTGCTCCAG    60
CCTAGGAGTC TACGGGGACC GCCTCCCGCG CCGCCACCAT GCCCAACTTC TCTGGCAACT   120
GGAAAATCAT CCGATCGGAA AACTTCGAGG AATTGCTCAA AGTGCTGGGG GTGAATGTGA   180
TGCTGAGGAA GATTGCTGTG GCTGCAGCGT CCAAGCCAGC AGTGGAGATC AAACAGGAGG   240
GAGACACTTT CTACATCAAA ACCTCCACCA CCGTGCGCAC CACAGAGATT AACTTCAAGG   300
TTGGGGAGGA GTTTGAGGAG CAGACTGTGG ATGGGAGGCC CTGTAAGAGC CTGGTGAAAT   360
GGGAGAGTGA GAATAAAATG GTCTGTGAGC AGAAGCTCCT GAAGGGAGAG GGCCCCAAGA   420
CCTCGTGGAC CAGAGAACTG ACCAACGATG GGAACTGAT  CCTGACCATG ACGGCGGATG   480
ACGTTGTGTG CACCAGGGTC TACGTCCGAG AGTGAGTGGC CACAGGTAGA ACCGCGGCCG   540
AAGCCCACCA CTGGCCATGC TCACCGCCCT GCTTCACTGC CCCCTCCGTC CCACCCCCTC   600
CTTCTAGGAT AGCGCTCCCC TTACCCCAGT CACTTCTGGG GGTCACTGGG ATGCCTCTTG   660
CAGGGTCTTG CTTTCTTTGA CCTCTTCTCT CCTCCCCTAC ACCAACAAAG AGGAATGGCT   720
GCAAGAGCCC AGATCACCCA TTCCGGGTTC ACTCCCCGCC TCCCCAAGTC AGCAGTCCTA   780
GCCCCAAACC AGCCCAGAGC AGGGTCTCTC TAAAGGGGAC TTGAGGGCCT GAGCAGGAAA   840
GACTGGCCCT CTAGCTTCTA CCCTTTGTCC CTGTAGCCTA TACAGTTTAG AATATTTATT   900
TGTTAATTTT ATTAAAATGC TTTA                                          924
```

(2) INFORMATION FOR SEQ ID NO:2:

(i) SEQUENCE CHARACTERISTICS:
(A) LENGTH: 138 amino acids
(B) TYPE: amino acid
(C) STRANDEDNESS: single
(D) TOPOLOGY: linear (ii) MOLECULE TYPE: peptide (iii) HYPOTHETICAL: YES (vi) ORIGINAL SOURCE:
(A) ORGANISM: homo sapien (x) PUBLICATION INFORMATION:
(A) AUTHORS: Astrom, Anders
Tavakkol, Amir
Pettersson, Ulrika
Cromie, Matthew
Elder, James T.

Voorhees, John J.
(B) TITLE: Molecular Cloning of Two Human Cellular
Retinoic Acid-Proteins (CRABP)
(C) JOURNAL: J. Biol. Chem.
(G) DATE: 1991
(K) RELEVANT RESIDUES IN SEQ ID NO:2: FROM 1 TO 138

(x) PUBLICATION INFORMATION:
(A) AUTHORS: Astrom, Anders
Tavakkol, Amir
Elder, James T.
Pettersson, Ulrika
Cromie, Matthew
Voorhees, John J.
(B) TITLE: Cloning of CRABPII cDNA from Human Skin:
Retinoic Acid Induces Expression of CRABPII but
Not CRABPI in Human Skin in Vivo and in Dermal but
Not Lung Fibroblasts in Vitro
(C) JOURNAL: J. Invest. Dermatol.
(D) VOLUME: 96
(F) PAGES: 547-547
(G) DATE: April-1991

(xi) SEQUENCE DESCRIPTION: SEQ ID NO:2:

| Met | Pro | Asn | Phe | Ser | Gly | Asn | Trp | Lys | Ile | Ile | Arg | Ser | Glu | Asn | Phe |
| 1 | | | | 5 | | | | | 10 | | | | | 15 | |

| Glu | Glu | Leu | Leu | Lys | Val | Leu | Gly | Val | Asn | Val | Met | Leu | Arg | Lys | Ile |
| | | | 20 | | | | | 25 | | | | | 30 | | |

| Ala | Val | Ala | Ala | Ala | Ser | Lys | Pro | Ala | Val | Glu | Ile | Lys | Gln | Glu | Gly |
| | | 35 | | | | | 40 | | | | | 45 | | | |

| Asp | Thr | Phe | Tyr | Ile | Lys | Thr | Ser | Thr | Thr | Val | Arg | Thr | Thr | Glu | Ile |
| | 50 | | | | | 55 | | | | | 60 | | | | |

| Asn | Phe | Lys | Val | Gly | Glu | Glu | Phe | Glu | Glu | Gln | Thr | Val | Asp | Gly | Arg |
| 65 | | | | | 70 | | | | | 75 | | | | | 80 |

| Pro | Cys | Lys | Ser | Leu | Val | Lys | Trp | Glu | Ser | Glu | Asn | Lys | Met | Val | Cys |
| | | | | 85 | | | | | 90 | | | | | 95 | |

| Glu | Gln | Lys | Leu | Leu | Lys | Gly | Glu | Gly | Pro | Lys | Thr | Ser | Trp | Thr | Arg |
| | | | 100 | | | | | 105 | | | | | 110 | | |

| Glu | Leu | Thr | Asn | Asp | Gly | Glu | Leu | Ile | Leu | Thr | Met | Thr | Ala | Asp | Asp |
| | | 115 | | | | | 120 | | | | | 125 | | | |

| Val | Val | Cys | Thr | Arg | Val | Tyr | Val | Arg | Glu |
| | 130 | | | | | 135 | | | |

(2) INFORMATION FOR SEQ ID NO:3:

(i) SEQUENCE CHARACTERISTICS:
(A) LENGTH: 525 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Homo Sapien
(F) TISSUE TYPE: skin
(G) CELL TYPE: fibroblast (vii) IMMEDIATE SOURCE:
(A) LIBRARY: human skin Lambda ZapII
(B) CLONE: lambda s3.1

(ix) FEATURE:
(A) NAME/KEY: CDS
(B) LOCATION: 8..418
(D) OTHER INFORMATION: /codon_start=8

( i x ) FEATURE:
    ( A ) NAME/KEY: 5'UTR
    ( B ) LOCATION: 1..7
    ( D ) OTHER INFORMATION: /citation=([1])

( i x ) FEATURE:
    ( A ) NAME/KEY: 3'UTR
    ( B ) LOCATION: 419..525
    ( D ) OTHER INFORMATION: /citation=([1])

( i x ) FEATURE:
    ( A ) NAME/KEY: terminator
    ( B ) LOCATION: 419..421
    ( D ) OTHER INFORMATION: /citation=([1])

( x ) PUBLICATION INFORMATION:
    ( A ) AUTHORS: Astrom, Anders
              Tavakkol, Amir
              Pettersson, Ulrika
              Cromie, Matthew
              Elder, James T.
              Voorhees, John J.
    ( B ) TITLE: Molecular Cloning of Two Human Cellular
            Retinoic Acid-Proteins (CRABP)
    ( C ) JOURNAL: J. Biol. Chem.
    ( G ) DATE: 1991
    ( K ) RELEVANT RESIDUES IN SEQ ID NO:3: FROM 1 TO 525

( x ) PUBLICATION INFORMATION:
    ( A ) AUTHORS: Astrom, Anders
              Tavakkol, Amir
              Elder, James T.
              Pettersson, Ulrika
              Cromie, Matthew
              Voorhees, John J.
    ( B ) TITLE: Cloning of CRABPII cDNA from Human Skin:
            Retinoic Acid Induces Expression of CRABPII but
            Not CRABPI in Human Skin in Vivo and in Dermal but
            Not Lung Fibroblasts in Vitro
    ( C ) JOURNAL: J. Invest. Dermatol.
    ( D ) VOLUME: 96
    ( F ) PAGES: 547-547
    ( G ) DATE: April-1991

( x i ) SEQUENCE DESCRIPTION: SEQ ID NO:3:

```
TGCCACCATG CCCAACTTCG CCGGCACCTG GAAGATGCGC AGCAGCGAGA ATTTCGACGA      60

GCTGCTCAAG GCACTGGGTG TGAACGCCAT GCTGAGGAAG GTGGCCGTAG CGGCTGCGTC     120

CAAGCCGCAC GTGGAGATCC GCCAGGACGG GGATCAGTTC TACATCAAGA CATCCACCAC     180

GGTGCGCACC ACTGAGATCA ACTTCAAGGT CGGAGAAGGC TTTGAGGAGG AGACCGTGGA     240

CGGACGCAAG TGCAGGAGTT TAGCCACTTG GGAGAATGAG AACAAGATCC ACTGCACGCA     300

AACTCTTCTT GAAGGGGACG GCCCCAAAAC CTACTGGACC CGTGAGCTGG CCAACGATGA     360

ACTTATCCTG ACGTTTGGCG CCGATGACGT GGTCTGCACC AGAATTTATG TCCGAGAGTG     420

AAGGCAGCTG GCTTGCTCCT ACTTTCAGGA AGGGATGCAG GCTCCCTGA  GGAATATGTC     480

ATAGTTCTGA GCTGCCAGTG GACCGCCCTT TTCCCCTACC AATAT                    525
```

( 2 ) INFORMATION FOR SEQ ID NO:4:

( i ) SEQUENCE CHARACTERISTICS:
        ( A ) LENGTH: 137 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( v i ) ORIGINAL SOURCE:

(A) ORGANISM: homo sapien (x) PUBLICATION INFORMATION:
    (A) AUTHORS: Astrom, Anders
            Tavakkol, Amir
            Pettersson, Ulrika
            Cromie, Matthew
            Elder, James T.
            Voorhees, John J.
    (B) TITLE: Molecular Cloning of Two Human Cellular
           Retinoic Acid-Proteins (CRABP)
    (C) JOURNAL: J. Biol. Chem.
    (G) DATE: 1991
    (K) RELEVANT RESIDUES IN SEQ ID NO:4: FROM 1 TO 137

(x) PUBLICATION INFORMATION:
    (A) AUTHORS: Astrom, Anders
            Tavakkol, Amir
            Elder, James T.
            Pettersson, Ulrika
            Cromie, Matthew
            Voorhees, John J.
    (B) TITLE: Cloning of CRABPII cDNA from Human Skin:
           Retinoic Acid Induces Expression of CRABPII but
           Not CRABPI in Human Skin in Vivo and in Dermal but
           Not Lung Fibroblasts in Vitro
    (C) JOURNAL: J. Invest. Dermatol.
    (D) VOLUME: 96
    (F) PAGES: 547-547
    (G) DATE: April-1991

(xi) SEQUENCE DESCRIPTION: SEQ ID NO:4:

```
Met Pro Asn Phe Ala Gly Thr Trp Lys Met Arg Ser Ser Glu Asn Phe
 1               5                  10                 15
Asp Glu Leu Leu Lys Ala Leu Gly Val Asn Ala Met Leu Arg Lys Val
             20                  25                 30
Ala Val Ala Ala Ala Ser Lys Pro His Val Glu Ile Arg Gln Asp Gly
         35                  40                 45
Asp Gln Phe Tyr Ile Lys Thr Ser Thr Thr Val Arg Thr Thr Glu Ile
     50                  55                 60
Asn Phe Lys Val Gly Glu Gly Phe Glu Glu Thr Val Asp Gly Arg
 65                  70                 75                 80
Lys Cys Arg Ser Leu Ala Thr Trp Glu Asn Glu Asn Lys Ile His Cys
             85                  90                 95
Thr Gln Thr Leu Leu Glu Gly Asp Gly Pro Lys Thr Tyr Trp Thr Arg
            100                 105                110
Glu Leu Ala Asn Asp Glu Leu Ile Leu Thr Phe Gly Ala Asp Asp Val
            115                 120                125
Val Cys Thr Arg Ile Tyr Val Arg Glu
            130                 135
```

(2) INFORMATION FOR SEQ ID NO:5:

(i) SEQUENCE CHARACTERISTICS:
        (A) LENGTH: 1322 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (F) TISSUE TYPE: Placenta (vii) IMMEDIATE SOURCE:

(A) LIBRARY: human placenta genomic library
(B) CLONE: lambda 2.1

(ix) FEATURE:
(A) NAME/KEY: TATA_signal
(B) LOCATION: 1008..1013

(ix) FEATURE:
(A) NAME/KEY: exon
(B) LOCATION: 1039..1245

(ix) FEATURE:
(A) NAME/KEY: intron
(B) LOCATION: 1246..1322

(x) PUBLICATION INFORMATION:
(A) AUTHORS: Astrom, Anders
Pettersson, Ulrika
Voorhees, John J
(B) TITLE: Structure of the human cellular retinoic
acid-binding protein II (CRABP-II) gene: Early
transcriptional regulation by retinoic acid
(C) JOURNAL: J. Biol. Chem.
(G) DATE: 1992
(K) RELEVANT RESIDUES IN SEQ ID NO:5: FROM 1 TO 1322

(xi) SEQUENCE DESCRIPTION: SEQ ID NO:5:

```
CTGCAGGAAG CCGTGCCCTC CTCCCACCCT CTTTGATCTC CCGTTTCAAA GCCGCTCTCC      60
AAGGGAGGGG AGGTCGCTCC TTCCGCCCGT TTTACAGCTC AGGATGGTGA CACCTGAGAC     120
CCTGCTCCGC CTTCTCCCCC GGCACCCATC CTCCGCCTA TCTAGGTGGT GGCGCAGCTC      180
GCCAGGGCTC CGCGCCTCTG TCCCCGCCTC CCTCCCTTCC CCCTACTGAG ACCCCTCGGG    240
GTCTCGGGAG TGAAGCGACA GAGAAAGCGT TTTAATAAAG ACCTTGCGTC AAGTGATTGG    300
CTGTGACCTC TGCCCTCCCA GCCTCGCGCC CTGGGCTCCT GCTTAACCCT TCAATGTCCG    360
CCCAGCGCAT TAAGGGGAGC GAGTCGCCTG GCGACTACTT CCAGAGTCCC CAGGCATTAC    420
GTGAGCCCGA AGCAGGGTGG AGGGGTGGGG GGACCGTGCC GCCCCGCCC AGCCTCTCCG      480
AGTTGTTCCA GCAGGGGCG CCGTTGCCTC ACTAGATCC CTAACCCCCG GAACCCCGCA       540
GCTCCCAAGC CCCTCTCTGA GTACGGAGTG GTCCACTGG ATCCAGTTCA GGGTTCAATG      600
GAGCTAGGGC CAGCTACGGC TCAAGATCTG GGTCCGCCT GCGGTGGGGT CGCCAGGTGT     660
CCGGCACCAA GGAGTTGAAT GCACCGAGTC AGGTTGGGGA TGGGTGGGGA ACAGGCGAGA    720
CGTGAGGAAC TCGGGTGGGG GACAGCCATA CACGAGCCCT GAGCATCTGC GCCCGCAGCT    780
AGCTCCCCCC GCCTCTGCGG AGAGCGCGAT TCAAGTGCTG GCTTTGCGTC CGCTTCCCCA    840
TCCACTTACT AGCGCAGGAG AAGGCTATCT CGGTCCCCAG AGAAGCCTGG ACCCACACGC    900
GGGCTAGATC CAGAGGTTGG TGGCGGGGGC GCAGGGCCCC AGGTGGGGGG GGGCGGAGCG    960
GGAGGCGGGG CCACTTCAAT CCTGGGCAGG GGCGGTTCCG TACAGGGTAT AAAAGCTGTC   1020
CGCGCGGGAG CCCAGGCCAG CTTTGGGGTT GTCCCTGGAC TTGTCTTGGT TCCAGAACCT   1080
GACGACCCGG CGACGGCGAC GTCTCTTTTG ACTAAAAGAC AGTGTCCAGT GCTCCAGCCT   1140
AGGAGTCTAC GGGGACCGCC TCCCGCGCCG CCACCATGCC CAACTTCTCT GGCAACTGGA   1200
AAATCATCCG ATCGGAAAAC TTCGAGGAAT TGCTCAAAGT GCTGGGTAAG GAAATGTTCG   1260
AGGGCCCAGG TGGGGCAAGG GGGGGCTCTG GAGTCCTCGA AGTTGGGGAT GAGAAAGACA   1320
GC                                                                  1322
```

(2) INFORMATION FOR SEQ ID NO:6:

(i) SEQUENCE CHARACTERISTICS:
(A) LENGTH: 1717 base pairs
(B) TYPE: nucleic acid ( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Homo sapiens
( F ) TISSUE TYPE: Placenta ( v i i ) IMMEDIATE SOURCE:
( A ) LIBRARY: human placenta genomic
( B ) CLONE: lambda 2.1

( i x ) FEATURE:
( A ) NAME/KEY: exon
( B ) LOCATION: 178..356

( i x ) FEATURE:
( A ) NAME/KEY: intron
( B ) LOCATION: 357..571

( i x ) FEATURE:
( A ) NAME/KEY: exon
( B ) LOCATION: 572..688

( i x ) FEATURE:
( A ) NAME/KEY: intron
( B ) LOCATION: 699..1152

( i x ) FEATURE:
( A ) NAME/KEY: exon
( B ) LOCATION: 1153..1618

( x ) PUBLICATION INFORMATION:
( A ) AUTHORS: Astrom, Anders
Pettersson, Ulrika
Voorhees, John J
( B ) TITLE: Structure of the human cellular retinoic-acid
binding protein (CRABP-II) gene: Early
transcriptional regulation by retinoic acid
( C ) JOURNAL: J. Biol. Chem.
( G ) DATE: 1992
( K ) RELEVANT RESIDUES IN SEQ ID NO:6: FROM 1 TO 1717

( x i ) SEQUENCE DESCRIPTION: SEQ ID NO:6:

```
CGCCTACCGT CTCCTTCAAG GCACTTTCTT AGACACCCGG GCACCAGGCA GATGCACCCC      60
CCAACACACC CACCCCAAGC AAGTCACAAA TCAGCCTGCT CCAACTGTCT TATGGGGAGG     120
GTGTGAGAGA GGTGCCCAAA GGCCCCTAAA AGGTGAGCCT CTCCTCTCTC CCCACAGGGG     180
TGAATGTGAT GCTGAGGAAG ATTGCTGTGG CTGCAGCGTC CAAGCCAGCA GTGGAGATCA     240
AACAGGAGGG AGACACTTTC TACATCAAAA CCTCCACCAC CGTGCGCACC ACAGAGATTA     300
ACTTCAAGGT TGGGGAGGAG TTTGAGGAGC AGACTGTGGA TGGGAGGCCC TGTAAGGTGA     360
GTGCCAGAAG GGGCTCCAGG GTCATGGCGT CATTGCCCTG CCTCTCAACC TGCCATTTTC     420
CAGGCTAGCA GTTAACTCCT AGCTTCTCTC TGTCCCAGTA GGGAAAATCC CTAGGTAGTG     480
GTGGGGGCTA GAAAGGGGCT CTCTCCCTTA TCCCTCTCAC TGCATTGCCC CTGCTATGGG     540
CCCAGCTCAC TTGGCCACCT GTCTCTTGCA GAGCCTGGTG AAATGGGAGA GTGAGAATAA     600
AATGGTCTGT GAGCAGAAGC TCCTGAAGGG AGAGGGCCCC AAGACCTCGT GGACCAGAGA     660
ACTGACCAAC GATGGGGAAC TGATCCTGGT AAGTCCTGCC TCCTCCCAC  TAATAGCAAA     720
CCCAGTGCTA CCTTCCAAGA TTCTCTGGGA GACCCCAGGG TGCAGGAGAC TCAAGAACAA     780
CCATGGCTGG ACTCCGCACC CTGCTGATGG GACTGCTTGA ACAGAACTAA GGTGTCCCTA     840
TCCCATACAG TGCCCTGTGT GAATTAGAAA TGGTGTTCCT TTTATGCAAG CAAAGGGCAT     900
```

| | | | | | |
|---|---|---|---|---|---|
| GTACTGAGGG | ATCCCAGCAG | TTCTTCAGGG | AGATCTTCCT | GGCTTGAGGA | GGAGGACGGG | 960
| CCCCAGGGCT | CTATTGCTAT | CCTCCCTCCA | TTGATGCCTG | GGCATTCTGG | GACCAGCTCC | 1020
| TGCCTGTTGG | TCTTGAGCCA | AGAAGCAGGT | TTGGACCTGG | AGGCCAAGCA | GAGTACCTCC | 1080
| ATTCAACCCT | CCTCTCCAAA | GCCACAGGAC | CCCAGGGGCC | TCTCAGGCTA | ACAACTACTT | 1140
| CTGTCCTTCC | AGACCATGAC | GGCGGATGAC | GTTGTGTGCA | CCAGGGTCTA | CGTCCGAGAG | 1200
| TGAGTGGCCA | CAGGTAGAAC | CGCGGCCGAA | GCCCACCACT | GGCCATGCTC | ACCGCCCTGC | 1260
| TTCACTGCCC | CCTCCGTCCC | ACCCCCTCCT | TCTAGGATAG | CGCTCCCCTT | ACCCCAGTCA | 1320
| CTTCTGGGGG | TCACTGGGAT | GCCTCTTGCA | GGGTCTTGCT | TTCTTTGACC | TCTTCTCTCC | 1380
| TCCCCTACAC | CAACAAAGAG | GAATGGCTGC | AAGAGCCCAG | ATCACCCATT | CCGGGTTCAC | 1440
| TCCCCGCCTC | CCCAAGTCAG | CAGTCCTAGC | CCCAAACCAG | CCCAGAGCAG | GGTCTCTCTA | 1500
| AAGGGGACTT | GAGGGCCTGA | GCAGGAAAGA | CTGGCCCTCT | AGCTTCTACC | CTTTGTCCCT | 1560
| GTAGCCTATA | CAGTTTAGAA | TATTTATTTG | TTAATTTTAT | TAAAATGCTT | TAAAAAAATA | 1620
| AAACCTGTCT | CTGGCTCATT | GGGCAGGTAG | ATAAGTCACC | TGAGTTCAAC | CTTGCCTCTG | 1680
| AAATGTAGTA | TGGGAAAGAC | TTGTGTTTCT | GCAGCAT | | | 1717

( 2 ) INFORMATION FOR SEQ ID NO:7:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| | | | | |
|---|---|---|---|---|
| GAATTCTAGA | CTGCCACCAT | GCCCAACTTC | GCCGGTACCT | GGAAGATG | 48

( 2 ) INFORMATION FOR SEQ ID NO:8:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | |
|---|---|---|---|---|---|
| CACTGGATCC | AAGCTGGCCA | CCTTTCACTC | CCGGACATAA | ATCCTCGTGC | A | 51

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| | | |
|---|---|---|
| CATCGGATCC | CAACTGGAAG | ATCATCCGA | 29

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:10:

CATCGGATCC CAACGTCATC TGCTGTCATT 30

( 2 ) INFORMATION FOR SEQ ID NO:11:

( i ) SEQUENCE CHARACTERISTICS:
( A ) LENGTH: 137 amino acids
( B ) TYPE: amino acid
( D ) TOPOLOGY: unknown ( i i ) MOLECULE TYPE: peptide ( x i ) SEQUENCE DESCRIPTION: SEQ ID NO:11:

| Met | Pro | Asn | Phe | Ala | Gly | Thr | Trp | Lys | Met | Arg | Ser | Ser | Glu | Asn | Phe |
|---|---|---|---|---|---|---|---|---|---|---|---|---|---|---|---|
| 1 | | | | 5 | | | | | 10 | | | | | 15 | |
| Asp | Glu | Leu | Leu | Lys | Ala | Leu | Gly | Val | Asn | Ala | Met | Leu | Arg | Lys | Val |
| | | | 20 | | | | | 25 | | | | | 30 | | |
| Ala | Val | Ala | Ala | Ala | Ser | Lys | Pro | His | Val | Glu | Ile | Arg | Gln | Asp | Gly |
| | | | 35 | | | | 40 | | | | | 45 | | | |
| Asp | Gln | Phe | Tyr | Ile | Lys | Thr | Ser | Thr | Thr | Val | Arg | Thr | Thr | Glu | Ile |
| | 50 | | | | | 55 | | | | | 60 | | | | |
| Asn | Phe | Lys | Val | Gly | Glu | Gly | Phe | Glu | Glu | Glu | Thr | Val | Asp | Gly | Arg |
| 65 | | | | | 70 | | | | | 75 | | | | | 80 |
| Lys | Cys | Arg | Ser | Leu | Pro | Thr | Trp | Glu | Asn | Glu | Asn | Lys | Ile | His | Cys |
| | | | | 85 | | | | | 90 | | | | | 95 | |
| Thr | Gln | Thr | Leu | Leu | Glu | Gly | Asp | Gly | Pro | Lys | Thr | Tyr | Trp | Thr | Arg |
| | | | 100 | | | | | 105 | | | | | 110 | | |
| Glu | Leu | Ala | Asn | Asp | Glu | Leu | Ile | Leu | Thr | Phe | Gly | Ala | Asp | Asp | Val |
| | | | 115 | | | | | 120 | | | | | 125 | | |
| Val | Cys | Thr | Arg | Ile | Tyr | Val | Arg | Glu | | | | | | | |
| | 130 | | | | | 135 | | | | | | | | | |

( 2 ) INFORMATION FOR SEQ ID NO:12:

( i ) SEQUENCE CHARACTERISTICS:
( A ) LENGTH: 138 amino acids
( B ) TYPE: amino acid
( D ) TOPOLOGY: unknown ( i i ) MOLECULE TYPE: peptide ( x i ) SEQUENCE DESCRIPTION: SEQ ID NO:12:

| Met | Pro | Asn | Phe | Ser | Gly | Asn | Trp | Lys | Ile | Ile | Arg | Ser | Glu | Asn | Phe |
|---|---|---|---|---|---|---|---|---|---|---|---|---|---|---|---|
| 1 | | | | 5 | | | | | 10 | | | | | 15 | |
| Glu | Glu | Met | Leu | Lys | Ala | Leu | Gly | Val | Asn | Met | Met | Met | Arg | Lys | Ile |
| | | | 20 | | | | | 25 | | | | | 30 | | |
| Ala | Val | Ala | Ala | Ala | Ser | Lys | Pro | Ala | Val | Glu | Ile | Lys | Gln | Glu | Asn |
| | | | 35 | | | | 40 | | | | | 45 | | | |
| Asp | Thr | Phe | Tyr | Ile | Lys | Thr | Ser | Thr | Thr | Val | Arg | Thr | Thr | Glu | Ile |
| | 50 | | | | | 55 | | | | | 60 | | | | |
| Asn | Phe | Lys | Ile | Gly | Glu | Glu | Phe | Glu | Glu | Gln | Thr | Val | Asp | Gly | Arg |
| 65 | | | | | 70 | | | | | 75 | | | | | 80 |
| Pro | Cys | Lys | Ser | Leu | Val | Lys | Trp | Glu | Ser | Gly | Asn | Lys | Met | Val | Cys |
| | | | | 85 | | | | | 90 | | | | | 95 | |
| Glu | Gln | Arg | Leu | Leu | Lys | Gly | Glu | Gly | Pro | Lys | Thr | Ser | Trp | Ser | Arg |
| | | | 100 | | | | | 105 | | | | | 110 | | |

```
        Glu  Leu  Thr  Asn  Asp  Gly  Glu  Leu  Ile  Leu  Thr  Met  Thr  Ala  Asp  Asp
                  115                      120                      125

Val  Val  Cys  Thr  Arg  Val  Tyr  Val  Arg  Glu
                  130                      135
```

( 2 ) INFORMATION FOR SEQ ID NO:13:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:13:

```
        Pro  Asn  Phe  Ala  Gly  Thr  Trp  Lys  Met  Arg  Ser  Ser  Glu  Asn  Phe  Asp
        1                 5                            10                       15

Glu  Leu  Leu  Lys  Ala  Leu  Gly  Val  Asn
                       20                      25
```

( 2 ) INFORMATION FOR SEQ ID NO:14:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:14:

```
        Thr  Asn  Phe  Leu  Glu  Asn  Trp  Lys  Ile  Ile  Xaa  Ser  Glu  Asn  Phe  Glu
        1                 5                            10                       15

Glu  Met  Leu  Lys  Ala  Leu  Gly  Val  Asn
                       20                      25
```

( 2 ) INFORMATION FOR SEQ ID NO:15:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:15:

```
        Pro  Asn  Phe  Ala  Gly  Thr  Trp  Lys  Met  Arg  Ser  Ser  Glu  Asn  Phe  Asp
        1                 5                            10                       15

Glu  Leu  Leu  Lys  Ala  Leu  Gly  Val  Asn
                       20                      25
```

( 2 ) INFORMATION FOR SEQ ID NO:16:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:16:

```
        Pro  Asn  Phe  Ser  Gly  Asn  Trp  Lys  Met  Arg  Ser  Ser  Glu  Asn  Phe  Glu
        1                 5                            10                       15

Glu  Leu  Leu  Lys  Ala  Leu  Gly  Val  Asn
                       20                      25
```

( 2 ) INFORMATION FOR SEQ ID NO:17:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:17:

TCAGGTCATG ACCTGATCAG GTCATGACCT GATCAGGTCA TGACCTGA  48

( 2 ) INFORMATION FOR SEQ ID NO:18:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

CTAGGCTGGA GCACTGGACA CTGTC  25